(12) United States Patent
Chester

(10) Patent No.: US 9,877,804 B2
(45) Date of Patent: Jan. 30, 2018

(54) ORTHODONTIC GRIPPING DEVICE

(75) Inventor: Neil Chester, Cambridge (CA)

(73) Assignee: Strite Industries Limited, Cambridge, Ontario (CA)

( * ) Notice: Subject to any disclaimer, the term of this patent is extended or adjusted under 35 U.S.C. 154(b) by 13 days.

(21) Appl. No.: 13/373,968

(22) Filed: Dec. 7, 2011

(65) Prior Publication Data
US 2012/0148974 A1 Jun. 14, 2012

Related U.S. Application Data

(60) Provisional application No. 61/457,013, filed on Dec. 8, 2010.

(51) Int. Cl.
*A61C 3/00* (2006.01)
*A61C 7/02* (2006.01)
*A61C 7/04* (2006.01)
*A61C 7/20* (2006.01)
*A61C 7/22* (2006.01)

(52) U.S. Cl.
CPC ............... *A61C 7/02* (2013.01); *A61C 7/04* (2013.01); *A61C 7/20* (2013.01); *A61C 7/22* (2013.01)

(58) Field of Classification Search
CPC .... A61C 7/02; A61C 7/22; A61C 7/20; A61C 7/04
USPC .................................. 433/8–11, 13, 20, 22, 2
See application file for complete search history.

(56) References Cited

U.S. PATENT DOCUMENTS

| 2,265,420 | A | 12/1941 | Brusse et al. |
| 3,084,437 | A | 4/1963 | Neger |
| 3,327,393 | A | 6/1967 | Brader |
| 3,477,129 | A | 11/1969 | Rubin |

(Continued)

FOREIGN PATENT DOCUMENTS

| CN | 1127465 A | 7/1996 |
| CN | 1190575 A | 8/1998 |

(Continued)

OTHER PUBLICATIONS

Zadno, Duerig. Linear and Non-Linear Superelasticity in NiTi. MRS Shape Memory Materials, (1989) vol. 9, [> serial < online], [retrieved on Aug. 9, 2013]. Retrieved from the Internet: http://www.nitinol.com/media/reference-library/074.pdf.*

(Continued)

*Primary Examiner* — Heidi M Eide
(74) *Attorney, Agent, or Firm* — Fasken Martineau Du Moulin LLP

(57) ABSTRACT

The present invention relates to an orthodontic gripping device having a body made of a superelastic metal alloy, cold worked titanium beta III, or solution heat treated and aged titanium beta III. The body has first and second, spaced apart arm portions connected to each other. Each arm portion includes a jaw portion having an inner, arch wire-gripping, surface. The inner gripping surfaces are disposed opposite one another in spaced relation with a station defined therebetween for receiving the arch wire. At least a portion of the station is sized smaller than the arch wire. The arm portions are resiliently deflectable outwardly away from each other to admit the arch wire into the station. Once seated in the station, the arch wire is tightly held by inner gripping surfaces so as to resist displacement of the gripping device relative to the arch wire.

49 Claims, 31 Drawing Sheets

(56) References Cited

U.S. PATENT DOCUMENTS

| | | |
|---|---|---|
| 3,683,502 A | 8/1972 | Wallshein |
| 4,197,643 A | 4/1980 | Burstone et al. |
| 4,216,583 A | 8/1980 | Reynolds |
| 4,227,876 A * | 10/1980 | Fogel et al. ............... 433/11 |
| 4,571,179 A | 2/1986 | Balenseifen |
| 4,909,735 A | 3/1990 | Wildman |
| 5,017,133 A | 5/1991 | Miura |
| 5,306,142 A | 4/1994 | Richards |
| 5,344,315 A * | 9/1994 | Hanson ............... 433/20 |
| 5,356,289 A | 10/1994 | Watanabe |
| 5,358,586 A * | 10/1994 | Schutz et al. ............... 148/671 |
| 6,957,957 B2 | 10/2005 | Pospisil |
| 7,140,876 B2 * | 11/2006 | Cinader et al. ............... 433/10 |
| 7,160,106 B2 | 1/2007 | Farzin-Nia et al. |
| 7,217,125 B2 * | 5/2007 | Lai et al. ............... 433/11 |
| 7,828,549 B1 | 11/2010 | Wildman |
| 2003/0118967 A1 * | 6/2003 | Tepper ............... A61C 7/14 433/11 |
| 2006/0003281 A1 | 1/2006 | Nicholson |
| 2006/0199137 A1 * | 9/2006 | Abels ............... A61C 7/12 433/11 |
| 2007/0042314 A1 | 2/2007 | Brosius |
| 2009/0004619 A1 | 1/2009 | Oda et al. |
| 2009/0017411 A1 | 1/2009 | Pospisil et al. |
| 2009/0017412 A1 | 1/2009 | Wool |
| 2010/0105000 A1 | 4/2010 | Scommegna et al. |
| 2010/0129764 A1 | 5/2010 | Pospisil |
| 2010/0129765 A1 | 5/2010 | Mohr et al. |
| 2010/0151403 A1 | 6/2010 | Tuneberg et al. |
| 2010/0285420 A1 | 11/2010 | Oda |
| 2010/0285421 A1 | 11/2010 | Heiser |
| 2011/0033811 A1 | 2/2011 | Swain |
| 2011/0033812 A1 | 2/2011 | Swain |
| 2011/0143301 A1 | 6/2011 | Maijer et al. |
| 2011/0151391 A1 | 6/2011 | Shih et al. |
| 2011/0183280 A1 | 7/2011 | Cosse et al. |
| 2011/0195371 A1 | 8/2011 | Hirsch |
| 2012/0028207 A1 * | 2/2012 | Cleary ............... A61C 7/00 433/10 |
| 2012/0231408 A1 * | 9/2012 | Lai et al. ............... 433/11 |

FOREIGN PATENT DOCUMENTS

| | | |
|---|---|---|
| CN | 101014296 A | 8/2007 |
| JP | S4421277 Y1 | 9/1969 |
| JP | S5850951 A | 3/1983 |
| JP | S61220643 A | 9/1986 |
| JP | H0626814 U | 4/1994 |
| WO | WO2009/023960 | 2/2009 |

OTHER PUBLICATIONS

Kejin Liu et al., A Non-Crimpable, JCO, Inc., 2010, pp. 693-695, vol. XLIV, No. 11, www.jco-online.com.*

Hao, Pengyu et al., Analysis on performances difference of NiTi orthodontics arch wires, Xihou Jinshu Cailiao Yu Gongehong/Rare Metal Materials and Engineering, vol. 37, No. 7, p. 1295-1298, Jul. 2008.*

Nikolai, RJ. et al., Orthodontic wire: a continuing evolution, Sep. 1997 3(3), 157-65, Graduate Department of Orthodontics, Saint Louis University Health Sciences Center, MO 63104, USA.*

Wang GH et al., Clinical study of Twin-wires on anchorage on canine retraction, *Shanghai Kou Qiang Yi Xue*, Jun. 2006, 15(3):332-4, Department of Stomatology, Shanghai Punio Central Hospital, Shanghai, China.*

Valiathan, Ashima, and Siddhartha, Dhas, Fiber reinforced composite arch-wires in orthodontics: Functions meets esthetics, Trends in Biomaterials and Artificial Organs, vol. 20, No. 1, p. 16-19, Jul. 2006.*

Raboud D.W. et al, Superelastic response of NiTi shape memory alloy wires for orthodontic applications, Smart Materials and Structures, vol. 9, No. 5, p. 684-692, Oct. 2000.*

International Preliminary Report on Patentability prepared in connection with International PCT Patent Application No. PCT/CA2011/001343, dated Apr. 11, 2013.

International Search Report prepared in connection with International PCT Patent Application No. PCT/CA2011/001343, dated Apr. 5, 2012.

Written Opinion of the International Searching Authority prepared in connection with International PCT Patent Application No. PCT/CA2011/001343, dated Apr. 12, 2012.

English translation of the office action issued by the Japanese Patent Office dated Oct. 6, 2015 against corresponding Japanese Patent Application No. 2013-542318.

Office Action issued by the State Intellectual Property Office of the People's Republic of China in connection with Chinese Patent Appln No. 2011800670239 dated May 5, 2015.

Search Report issued by the State Intellectual Property Office of the People's Republic of China in connection with Chinese Patent Appln No. 2011800670239 dated Apr. 24, 2015.

Office action issued by the Japanese Patent Office dated Oct. 6, 2015 against corresponding Japanese Patent Application No. 2013-542318, along with an English language summary.

Supplementary European Search Report dated Apr. 20, 2016 against corresponding European Patent Application No. 11846451.0.

Second Office Action dated Nov. 13, 2015 against corresponding Chinese Patent Application No. 2011800670239 and English translation thereof.

* cited by examiner

ORTHODONTIC GRIPPING DEVICE

CROSS-REFERENCE APPLICATIONS

The present invention claims priority under 35 U.S.C. §120 to U.S. Provisional Patent Application No. 61/457,013, filed on Dec. 8, 2010, the disclosure of which is incorporated by reference herein in its entirety.

FIELD OF THE INVENTION

The present invention relates to the field of orthodontics, in particular, to an orthodontic gripping device suitable for tightly clamping onto an arch wire or other orthodontic component.

BACKGROUND OF THE INVENTION

In orthodontics, an arch wire is used in conjunction with orthodontic brackets mounted to the patient's teeth to move the teeth to desired positions. The arch wire is configured to conform generally to the dental arch of the patient and is accommodated or seated within arch wire slots defined in the orthodontic brackets. The arch wire exerts forces on the orthodontic brackets which over time cause the teeth to move to their correct positions.

In orthodontic treatment, it is customary to place arch wire stops at specific locations on the arch wire to prevent displacement of the arch wire in the mesial/distal direction relative to one or more brackets. In some instances, arch wire stops will be provided to arrest movement at the free ends of the arch wire to prevent the arch wire from disengaging from the arch wire slot of the distalmost bracket and from making contact with (and possibly, irritating) the soft tissue (e.g. gums) in the patient's mouth. In other instances, stops may be used to fix the arch wire to a bracket/tooth combination to effect a particular transmission of forces to the bracket/tooth combination to achieve a particular result (e.g. to prevent migration of a tooth along the arch wire).

The arch wire stops that have been developed to date use a variety of techniques and/or structural components to limit mesial/distal displacement of the arch wire relative to a bracket. One known design employs a generally C-shaped clamp provided with an arch wire receiving slot. A closure member is pivotally connected to the clamp and can be moved between an open position to allow access to the arch wire receiving slot and a closed position wherein access to the arch wire receiving is restricted. The closure member has a variable thickness and is formed with an inner camming surface for engagement with the arch wire. When the closure member is moved to the open position, the arch wire receiving slot remains unobstructed and can receive an arch wire. When the closure member is moved to the closed position, the inner camming surface is brought to bear against the outer surface of the arch wire and creates a mechanical constriction (or narrowing) of the arch wire slot. As a result, the arch wire is retained between the inner walls of the clamp and the inner camming surface, and is discouraged from moving mesially or distally relative to a bracket by the friction forces acting on the arch wire.

Still other stops use different movable components to tightly hold the arch wire within the stop. For example, in some stops, a rotatable screw is threadingly engaged with a sleeve so as to project into the arch wire slot defined in the sleeve. As the screw is tightened, its lingual end bears against the outer surface of the arch wire trapping it within the sleeve.

The relatively small size of these types of stops and the fact that they include movable components have tended to make them difficult to handle and deploy in the field. Moreover, there have been some complaints that once mounted in the mouth these stops tend to be bulky and may irritate the patient's cheek or gum tissue as a result of their bulkiness. The design of these stops may also allow food to become trapped within the stop or between the stop and the patient's soft tissue or dentition. Additionally, these stops tend to loosen from, or slip along, the arch wire over time.

A more common approach to restricting mesial/distal displacement of an arch wire involves the use of crimpable, tubular or C-shaped, sleeves. The arch wire is inserted through the sleeve and its position is fixed relative to the arch wire by crimping the sleeve in place. Slippage problems have been encountered with these types of stops, as the arch wire tends to slide within the sleeve when forces are applied to it. To address these concerns, some sleeves have been provided with roughened or irregular inner wire-engaging surfaces to increase friction and enhance the gripping action of the sleeve. These roughened surfaces may be obtained by coating the inner wire-engaging surfaces with abrasive material or by mechanically roughening the surfaces. These modifications have tended to lessen the occurrence of slippage of the arch wire. However, handling and slippage problems remain. Threading of the arch wire through the sleeve can be challenging as the arch wire itself has a relatively small cross-sectional area and the passageway formed in the sleeve is also quite small. Once threaded on the arch wire (and prior to crimping) the sleeve can inadvertently move during crimping thus making precise positioning difficult.

In light of the foregoing, it would be advantageous to have an orthodontic gripping device or arch wire stop with enhanced gripping action to overcome the slippage problems heretofore experienced with existing arch wire stops. Preferably, such an arch wire gripping device would be relatively easy to handle and quick to attach on an arch wire.

SUMMARY OF THE INVENTION

According to a broad aspect of an embodiment of the present invention, there is provided an orthodontic gripping device for attaching to an arch wire. The gripping device includes a body made of a material selected from the group consisting of a superelastic metal alloy, cold worked titanium beta III, and solution heat treated and aged titanium beta III. The body has first and second, spaced apart arm portions connected to each other. The first arm portion includes a first jaw portion having a first inner, arch wire-gripping surface. The second arm portion includes a second jaw portion having a second inner, arch wire-gripping surface. The first and second inner gripping surfaces are disposed opposite one another in spaced relation. The space between the first and second inner gripping surfaces defines a station for receiving the arch wire therein. At least a portion of the arch wire receiving station is sized smaller than the arch wire. The body further includes an entranceway defined between the first and second arm portions. The entranceway provides access to the arch wire receiving station. The first and second arm portions are resiliently deflectable outwardly away from each other when the arch wire is admitted through the entranceway into the arch wire receiving station. The first and second inner gripping surfaces engage the arch wire and apply opposing gripping forces against the arch wire so as to resist displacement of the gripping device relative to the arch wire, when the arch wire is seated within the arch wire receiving station.

In another feature, the body is of unitary construction. In a further alternative, at least one of the arm portions is a separate component. Optionally, the superelastic metal alloy may be selected from the group consisting of: (a) cold worked nickel titanium; (b) cold worked and aged nickel titanium; (c) cold worked nickel titanium and other alloying elements; and (d) cold worked and aged nickel titanium and other alloying elements. In one feature, the superelastic metal alloy behaves in a linear superelastic mode. In another feature, the superelastic metal alloy behaves in a non-linear superelastic mode. In alternative feature, the body is made of a material consisting of: (a) cold worked titanium beta III; and (b) solution heat treated and aged titanium beta III.

In an additional feature, the body has a longitudinal centerline. The first and second arm portions are disposed on opposite sides of the longitudinal centerline and are mirror images of each other.

In yet another feature, the body has a longitudinal centerline and the body is symmetrical about the longitudinal centerline. Alternatively, the body may be asymmetrical about the longitudinal centerline. In still another feature, the body has a transverse centerline and is symmetrical about the transverse centerline. In a further alternative feature, the body may be asymmetrical about the transverse centerline.

In one feature, the body further includes a base portion extending between the first and second arm portions to connect one to the other. The entranceway is disposed opposite the base portion.

In another feature, the arch wire has a profile defined by an outer surface. The first and second gripping surfaces are configured to substantially conform to at least a portion of the arch wire's outer surface. Additionally, the profile of the arch wire is generally circular. Each of the first and second inner gripping surfaces has an arcuate profile configured to at least partially match the curvature of the arch wire's profile. In a further feature, the arch wire has a diameter. The arch wire receiving station has a substantially circular profile and a diameter. The diameter of the arch wire receiving station is sized smaller than the diameter of the arch wire.

In yet another feature, the arch wire has a width. At least a portion of the arch wire receiving station is sized smaller than the width of the arch wire. Optionally, the arch wire receiving station may have a width of constant dimension. The width of the arch wire receiving station could be sized smaller than the width of the arch wire. In addition, the body has a longitudinal centerline. The first and second arm portions are disposed on opposite sides of the longitudinal centerline. The first and second arm portions are mirror images of each other. The first and second inner gripping surfaces are oriented substantially parallel to the longitudinal centerline.

In an optional feature, the arch wire has a width. The arch wire receiving station has a width of variable dimension. The smallest width of the arch wire receiving station is sized smaller than the width of the arch wire. The body has a longitudinal centerline. The first and second arm portions are disposed on opposite sides of the longitudinal centerline and are mirror images of each other. The first and second inner gripping surfaces have a skewed orientation relative to the longitudinal centerline. Each gripping surface converges toward the other in the direction of the entranceway.

In an additional feature, each inner gripping surface is a surface selected from the group consisting of: (a) a smooth surface; (b) an irregular surface; (c) a textured surface; and (d) a surface coated with a friction enhancing material.

In a further feature, the entranceway is funnel-shaped and tapers in the direction of the arch wire receiving station. The entranceway terminates in a throat and the throat is sized smaller than the size of the arch wire. In one optional feature, the throat is sized between 35% and 40% of the diameter of the arch wire. In another optional feature, the throat is sized between 65% and 70% of the width of the arch wire.

In still another feature, the gripping device further includes an orthodontic accessory formed in the body. The orthodontic accessory is selected from the group consisting of: (a) a hook; (b) an auxiliary slot; and (c) an eyelet. In another feature, the gripping device further includes a hook extending from the body. Optionally, the hook may be integrally formed with the body. In another feature, the hook is carried on the first arm portion. The first arm portion has an outer surface. The hook may extend perpendicular to the outer surface of the first arm portion, or alternatively, the hook may extend from the outer surface of the first arm portion on a slant.

In yet another feature, the body further includes a base portion extending between the first and second arm portions to connect one to the other. The hook is carried on the base portion. The base portion has an outer surface. The hook may extend perpendicular to the outer surface of the base portion or alternatively, the hook may extend from the outer surface of the base portion on a slant.

In still another feature, the body further includes an outer surface and the hook extends from the outer surface of the body.

In a further feature, the arch wire receiving station is shaped to accommodate an arch wire having a profile selected from the group consisting of (a) a circular profile; (b) a rectangular profile; (c) a square profile; and (d) a D-shaped profile.

In yet another feature, the gripping device is provided with means for facilitating handling of the gripping device. The handling means is formed on the body. More specifically, the handling means includes a first groove defined in the outer surface of the first arm portion and a second groove defined in the outer surface of the second arm portion. The first groove is disposed opposite the second groove. In another feature, the handling facilitating means includes first and second lateral wing members extending from the base portion. the first lateral wing member is disposed in spaced relation relative to the first arm portion. The second lateral wing member is disposed in spaced relation relative to the second arm portion. In a further feature, each of the first and second lateral wing members has an outer lateral surface and is moveable between an undeflected position and a deflected position. The gripping device has a width measured between the outer lateral surface of the first lateral wing member and the outer lateral surface of the second lateral wing member. The width of the gripping device when the first and second lateral wing members are in the deflected position is smaller than the width of the gripping device when the first and second lateral wing members are in the undeflected position.

In an additional feature, the arch wire receiving station has a profile selected from the group consisting of: (a) a circular profile; (b) an oval profile; (c) a rectangular profile; (d) a square profile; and (e) a quatrefoil profile.

In one feature, the body has a longitudinal centerline. The arch wire receiving station has a substantially oval profile defined by a major axis and a minor axis. The minor axis is disposed parallel to the longitudinal centerline. In another feature, the arch wire has a diameter and the arch wire receiving station has a diameter measured along the minor axis. The diameter of the arch wire receiving station measured along the minor axis is sized smaller than the diameter of the arch wire.

According to a broad aspect of another embodiment of the present invention, there is provided an orthodontic gripping device for attaching to an arch wire. The gripping device includes a body made of a shape memory material having a shape reset temperature range within which the shape memory material is capable of deforming significantly from a memorized shape of the shape memory material and a shape recovery temperature range within which the shape memory material is capable of recovering the memorized shape. The body has first and second, spaced apart arm portions connected to each other. The first arm portion includes a first jaw portion having a first inner, arch wire-gripping surface. The second arm portion includes a second jaw portion having a second inner, arch wire-gripping surface. The first and second inner gripping surfaces are disposed opposite one another in spaced relation. The space between the first and second inner gripping surfaces defines a station for receiving the arch wire therein. At least a portion of the arch wire receiving station is sized smaller than the arch wire. The body further includes an entranceway defined between the first and second arm portions. The entranceway provides access to the arch wire receiving station. The first and second arm portions are movable outwardly away from each other when the temperature of the shape memory material of the body lies within the shape reset temperature range and remain spread apart as long as the temperature of the shape memory material lies below the shape recovery temperature range, so as to allow admission of the arch wire through the entranceway into the arch wire receiving station. The first and second inner gripping surfaces engage the arch wire and apply opposing gripping forces against the arch wire so as to resist displacement of the gripping device relative to the arch wire, when the arch wire is seated within the arch wire receiving station and the temperature of the shape memory material of the body lies within the shape recovery temperature range.

In an additional feature, the shape memory material is selected from the group consisting of: (a) a shape memory metal alloy; and (b) a shape memory non-metallic material. In another feature, the shape recovery temperature range of the shape memory material lies below the temperature of a patient's oral cavity. In further feature, the shape recovery temperature range of the shape memory material encompasses the temperature of a patient's oral cavity. In an alternate feature, the shape recovery temperature range of the shape memory material is above the temperature of a patient's oral cavity and the shape reset temperature range of the shape memory material lies below the temperature of a patient's oral cavity.

According to a broad aspect of another embodiment of the present invention, there is provided an orthodontic gripping device for attaching to an arch wire. The gripping device includes a body which has first and second, spaced apart arm portions connected to each other. The first arm portion includes a first jaw portion having a first inner, arch wire-gripping surface. The second arm portion includes a second jaw portion having a second inner, arch wire-gripping surface. The first and second inner gripping surfaces are disposed opposite one another in spaced relation. The space between the first and second inner gripping surfaces defines a station for receiving the arch wire therein. At least a portion of the arch wire receiving station is sized smaller than the arch wire. The body further includes an entranceway defined between the first and second arm portions. The entranceway provides access to the arch wire receiving station. The first and second arm portions are resiliently deflectable outwardly away from each other when the arch wire is admitted through the entranceway into the arch wire receiving station. The first and second inner gripping surfaces engage the arch wire and apply opposing gripping forces against the arch wire so as to resist displacement of the gripping device relative to the arch wire, when the arch wire is seated within the arch wire receiving station. In a further feature, the body is made of a resilient spring-back material.

According to a broad aspect of still another embodiment of the present invention, there is provided an orthodontic arch wire kit. The kit includes an arch wire and a gripping device for attaching to an arch wire. The gripping device includes a body made of a material selected from the group consisting of a superelastic metal alloy, cold worked titanium beta III, and solution heat treated and aged titanium beta III. The body has first and second, spaced apart arm portions connected to each other. The first arm portion includes a first jaw portion having a first inner, arch wire-gripping surface. The second arm portion includes a second jaw portion having a second inner, arch wire-gripping surface. The first and second inner gripping surfaces are disposed opposite one another in spaced relation. The space between the first and second inner gripping surfaces defines a station for receiving the arch wire therein. At least a portion of the arch wire receiving station is sized smaller than the arch wire. The body further includes an entranceway defined between the first and second arm portions. The entranceway provides access to the arch wire receiving station. The first and second arm portions are resiliently deflectable outwardly away from each other when the arch wire is admitted through the entranceway into the arch wire receiving station. The first and second inner gripping surfaces engage the arch wire and apply opposing gripping forces against the arch wire so as to resist displacement of the gripping device relative to the arch wire, when the arch wire is seated within the arch wire receiving station.

In another feature, the arch wire has a cross-sectional profile selected from the group consisting from: (a) circular; (b) rectangular; (c) square; and (d) D-shaped. In one optional feature, the arch wire is selected from the group consisting of: (a) braided wire strands; (b) helically wrapped strands. Additionally, the arch wire could be selected from the group consisting of: (a) a multi-strand arch wire with a core; and (b) a multi-strand coreless arch wire. In another optional feature, the arch wire is a single solid wire.

In still another feature, the arch wire is made of material selected from the group consisting of: (a) a linear elastic material; (b) a superelastic material; and (c) a shape memory material.

According to a broad aspect of yet another embodiment of the present invention, there is provided a dental gripping device for attaching to a dental component. The gripping device includes a body made of a material selected from the group consisting of a superelastic metal alloy, cold worked titanium beta III, and solution heat treated and aged titanium beta III. The body has first and second, spaced apart arm portions connected to each other. The first arm portion includes a first jaw portion having a first inner gripping surface. The second arm portion includes a second jaw portion having a second inner gripping surface. The first and second inner gripping surfaces are disposed opposite one another in spaced relation. The space between the first and second inner gripping surfaces defines a station for receiving the dental component. At least a portion of the receiving station is sized smaller than the dental component. The body further includes an entranceway defined between the first and second arm portions. The entranceway provides access to the receiving station. The first and second arm portions are resiliently deflectable outwardly away from each other when the dental component is admitted through the entranceway into the receiving station. The first and second inner gripping surfaces engages the dental component and applies opposing gripping forces against the dental component so as to resist displacement of the gripping device relative to the dental component, when the dental component is seated within the receiving station.

According to a broad aspect of still another embodiment of the present invention, there is provided a gripping device for attaching to an object to be gripped. The gripping device includes a body made of a material selected from the group consisting of a superelastic material, cold worked titanium beta III, and solution heat treated and aged titanium beta III. The body has first and second, spaced apart arm portions connected to each other. The first arm portion includes a first jaw portion having a first inner gripping surface. The second arm portion includes a second jaw portion having a second inner gripping surface. The first and second inner gripping surfaces are disposed opposite one another in spaced relation. The space between the first and second inner gripping surfaces defines a station for receiving the object to be gripped. At least a portion of the receiving station is sized smaller than the object to be gripped. The body further includes an entranceway defined between the first and second arm portions. The entranceway provides access to the receiving station. The first and second arm portions are resiliently deflectable outwardly away from each other when the object to be gripped is admitted through the entranceway into the receiving station. The first and second inner gripping surfaces engages the object to be gripped and applies opposing gripping forces against the object to be gripped so as to resist displacement of the gripping device relative to the object to be gripped, when the object to be gripped is seated within the receiving station.

BRIEF DESCRIPTION OF THE DRAWINGS

The embodiments of the present invention shall be more clearly understood with reference to the following detailed description of the embodiments of the invention taken in conjunction with the accompanying drawings, in which.

DETAILED DESCRIPTION OF EMBODIMENTS OF THE INVENTION

Figure 1:
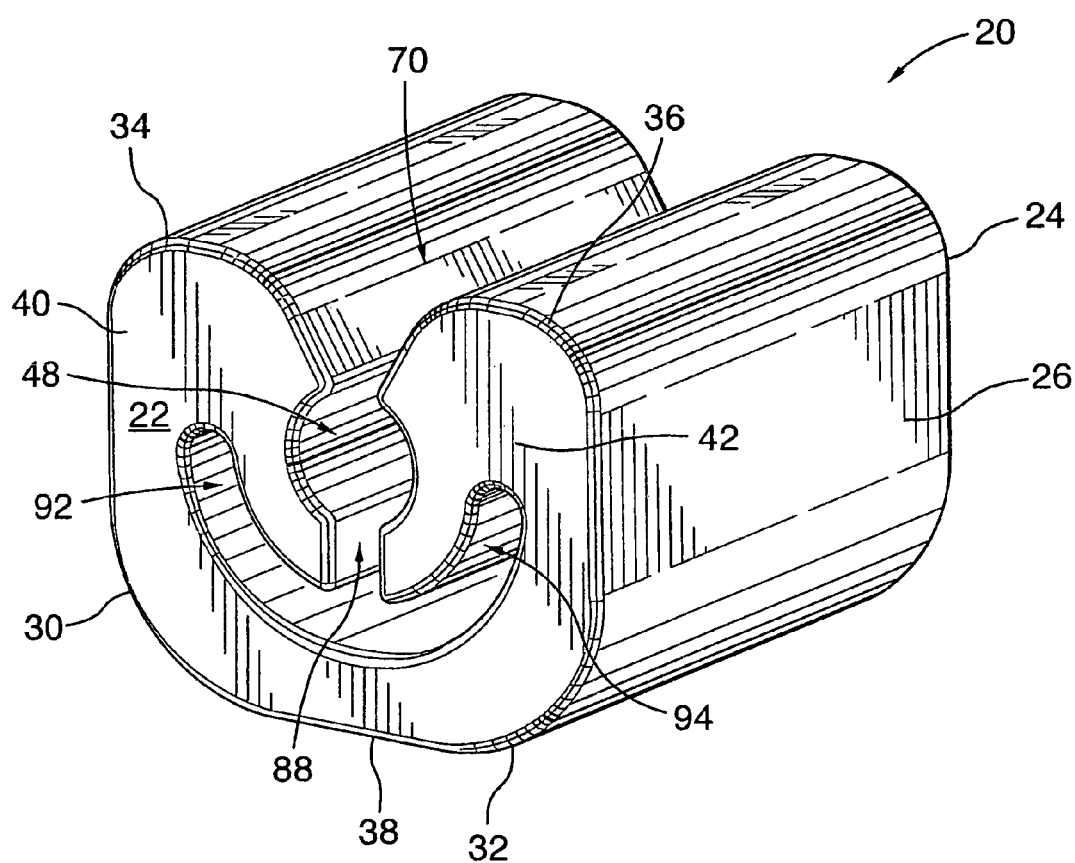
FIG. 1 is a perspective view of an orthodontic gripping device in accordance with a first embodiment of the invention.

The description, which follows, and the embodiments described therein are provided by way of illustration of an example, or examples of particular embodiments of principles and aspects of the present invention. These examples are provided for the purposes of explanation and not of limitation, of those principles of the invention. In the description that follows, like parts are marked throughout the specification and the drawings with the same respective reference numerals.

As used in this specification, the term "superelastic material" is understood to mean a material acting or behaving in a linear superelastic mode or in a non-linear superelastic mode. Similarly, a "superelastic metal alloy" means a metal alloy acting or behaving in a linear superelastic mode or in a non-linear superelastic mode. In the context of this specification, a material is considered to behave in a linear superelastic mode when it is able to undergo strains approximately 4%, without incurring excessive permanent set after unloading, all the time exhibiting a substantially linear relationship between stress and strain. A material is considered to behave in a non-linear superelastic mode when it exhibits the ability to incur relatively large amounts of strain without incurring excessive permanent set after unloading, and the loading and unloading stress-strain curves for the material are non-linear or multi-linear for the majority of their extent.

The term "shape memory material" is understood to mean a material acting or behaving in a shape memory mode. In like fashion, a "shape memory metal alloy" means a metal alloy acting or behaving in a shape memory mode. In the context of this specification, a material is considered to behave in a shape memory mode when it has the ability to both undergo deformation of a previously memorized shape and subsequently recover that memorized shape when exposed to some type of external stimulus, most commonly a reversible temperature change (as is the case, when the material is a metal alloy).

Figure 2A:
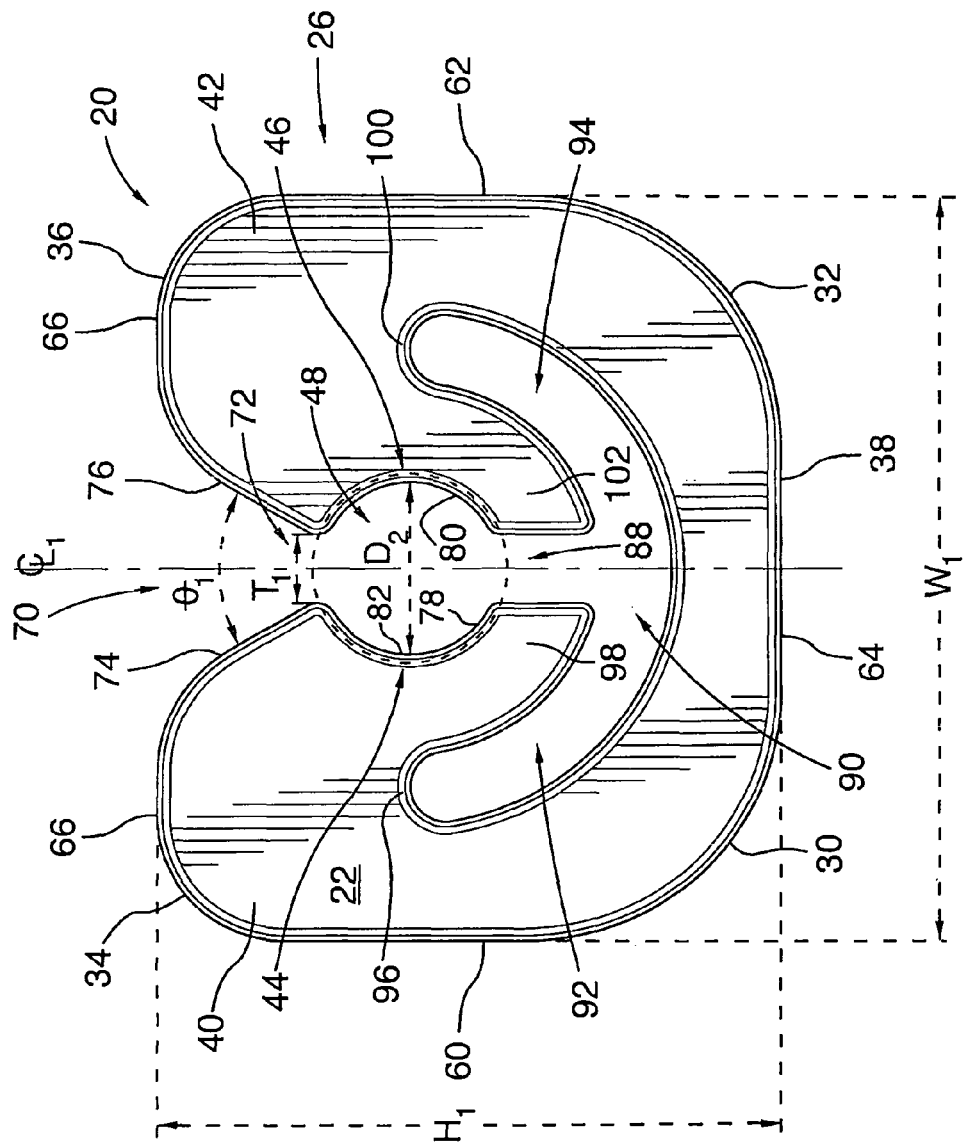
FIG. 2A is an end elevation (or mesial) view of the orthodontic gripping device shown in FIG. 1.
Figure 2B:
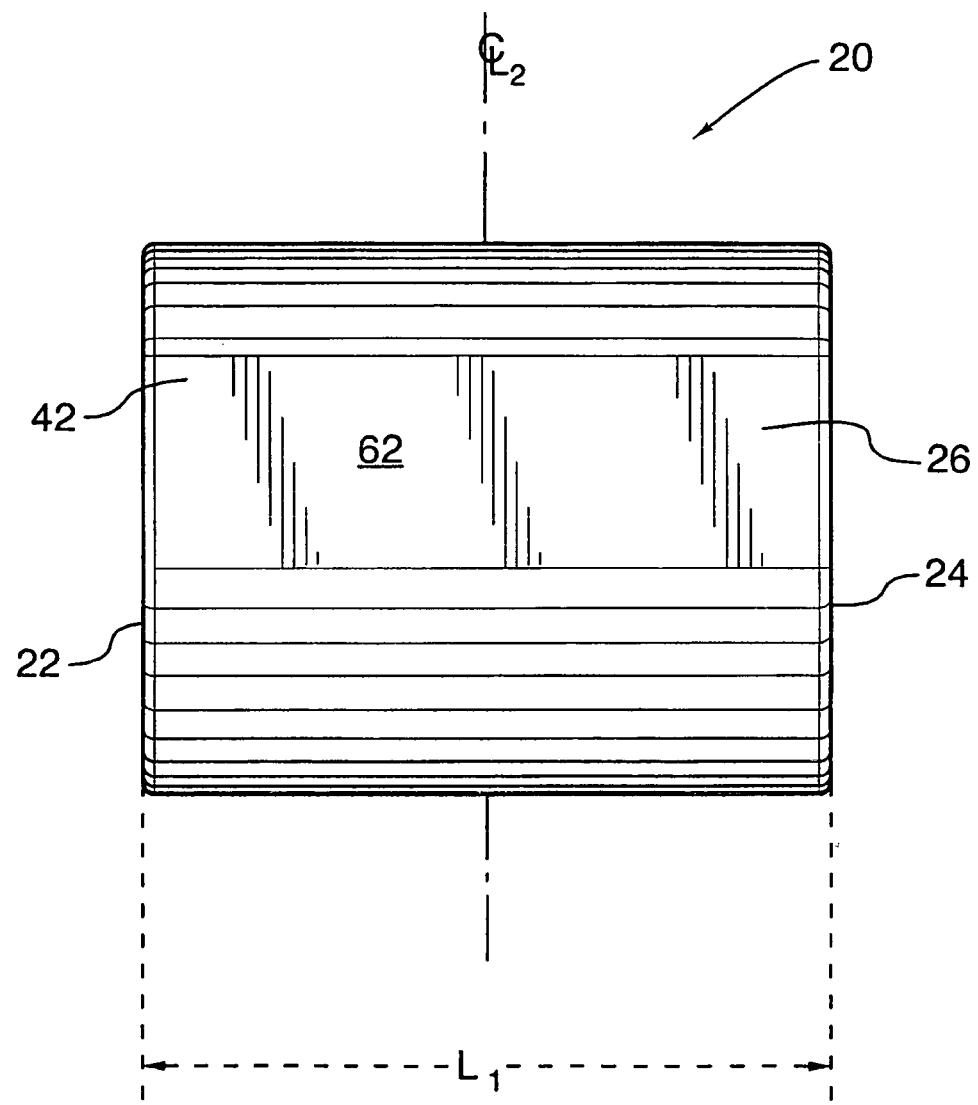
FIG. 2B is a side elevation view of the orthodontic gripping device shown in FIG. 1.

Referring to FIGS. 1, 2A and 2B, there is shown an orthodontic gripping device in accordance with a first embodiment of the present invention designated generally with reference numeral 20. The gripping device 20 is configured for use with an orthodontic arch wire. The orthodontic gripping device 20 includes a mesial face 22, a distal face 24 and an elongate body 26 extending between the mesial and distal faces 22 and 24. In this embodiment, the body 26 is of unitary (one-piece or monolithic) construction fabricated from a superelastic material. Preferably, such material is a superelastic metal alloy. Most preferably, the superelastic metal alloy is nickel titanium, or nickel titanium and other alloying elements (e.g. chromium (Cr), iron (Fe), vanadium (V), aluminium (Al), copper (Cu), cobalt (Co)), such as nickel/titanium/copper or nickel/titanium/copper/chromium. Preferably, the nickel titanium, or nickel titanium and other alloying elements, is cold worked. Although, cold worked and aged nickel titanium or cold worked and aged nickel titanium and other alloying elements, could also be used. In this embodiment, the gripping device 20 is made of cold worked nickel titanium.

However, it should be appreciated that the gripping device could also be made from other materials suitable for use in orthodontic appliances and exhibiting spring-back properties similar to those exhibited by superelastic materials. For example, a gripping device fabricated from cold worked titanium beta III or solution heat treated and aged titanium beta III (a titanium molybdenum alloy) has been found to have superior gripping strength. Testing has shown that the gripping device could also be made of cold worked ELGILOY™ alloy (a cobalt, chromium and nickel alloy). Still other materials may be selected based on their ability to resist permanent deformation and/or mechanical failure when the gripping device is flexed during its engagement with the arch-wire, while at the same time possessing sufficient material stiffness, such that the gripping device exhibits sufficient spring-back to hold the arch-wire firmly in place once the gripping device is fully engaged with the arch wire.

In still other embodiments, the gripping device could be made of a shape memory material, such a shape memory metal alloy. Although, conceivably, a non-metallic material (such as a polymer) possessing shape memory properties could also be used.

For reasons of strength and robustness, it is generally preferred that the body be made monolithic. However, in certain applications it may be desirable to have the body fabricated from separate components. These components could all be made of the same superelastic or shape memory material. Alternatively, the body could be made of a composite of superelastic materials or a composite of shape memory materials. In a further alternative embodiment, the body could be made of a composite of one or superelastic materials with a non-superelastic material or a composite of one or more shape memory materials with a non-shape memory material.

Preferably, the orthodontic gripping device is manufactured using material removal techniques. However, it is possible the gripping device could also be fabricated using other manufacturing techniques, such as rapid prototyping, sintering, casting, extrusion etc. In cases, where the body is made of separate components, each of these components could be made using one of the afore-mentioned methods or the like and subsequently assembled to each other to form the body by laser welding, fusing, or other similar process.

The body 26 has a vaguely rectangular shape or profile when seen in a mesial view such as shown in FIG. 2A. The shape of the body 26 is defined substantially by four smoothly radiused corners—first corner 30, second corner 32, third corner 34 and fourth corner 36. The corners 30, 32, 34 and 36 are rounded so as to avoid the formation of abrupt projecting edges which could otherwise irritate the soft tissue in the patient's mouth and cause discomfort when the orthodontic gripping device 20 is deployed in the patient's mouth.

The body 26 includes a longitudinal centreline $CL_1$ (shown in FIG. 2A), a base portion 38 and a pair of opposed, spaced apart, first and second arm portions 40 and 42 connected to the base portion 38 and disposed on opposite sides of the longitudinal centerline $CL_1$. The body 26 is symmetrical about the longitudinal centerline $CL_1$ such that the arm portions 40 and 42 are mirror images of each other. The body 26 is also configured to be symmetrical about a transverse centerline $CL_2$ (shown in FIG. 2B). This need not be the case in every application. In other embodiments, the body could be configured asymmetrically about one or both the longitudinal centerline $CL_1$ and the transverse centerline $CL_2$.

The first arm portion 40 joins the base portion 38 at the first corner 30, while the second arm portion 42 attaches to the base portion 38 at the second corner 32. Each arm portion 40, 42 extends away from corner 30, 32, respectively, in a direction generally perpendicular to the base portion 38. At the third corner 34, the first arm portion 40 turns inwardly toward the second arm portion 42 and ultimately, terminates with a first arch wire engaging jaw portion 44. Similarly, the second arm portion 42 turns inwardly toward the first arm portion 40 at the fourth corner 36 to terminate with a second arch wire engaging jaw portion 46.

As shown in FIG. 2A, the first and second jaw portions 44 and 46 are arranged opposite one another and are separated by a relatively small gap which defines an arch wire receiving slot or station 48 for captively engaging (securely retaining) an arch wire 50 therein. Configured in this manner, the first and second jaw portions 44 and 46 together define the gripping jaw 52 of the orthodontic gripping device 20.

While in the preferred embodiment, the body 26 is formed with two opposed arm portions 40 and 42 joined to and integrally formed with the base portion 38, in other embodiments, the body could be configured differently. For instance, one or both of the arm portions could be fabricated as separate components that are subsequently fixed to the base portion.

In another embodiment, the body could have two pairs of arms portions mounted in opposition to each other. In such an embodiment, a first pair of arm portions would include first and second, spaced apart, arm portions spaced side-by-side. Similarly, the second pair of arm portions would include third and fourth, spaced apart, arm portions spaced side-by-side. The first arm portion would be disposed opposite the third arm portion, while the second arm portion would be arranged opposite the fourth arm portion. Each of these arm portions would possess an arch wire engaging jaw portion. Defined between the jaw portions of the first and second arm portions, and the jaw portions of the third and fourth arm portions, would be arch wire receiving slots or stations for captively engaging (securely retaining) an arch wire therein. Configured in this manner, the jaw portions of the first and second arm portions together would define a first gripping jaw, while the jaw portions of the third and fourth arm portions together would define a second gripping jaw. In still other embodiments, more than two pairs of opposed arm portions may be provided. Moreover, the body could also be configured so that two or more, smaller arm portions are mounted in opposition to a single, larger arm portion.

Still other modifications may be brought to the body. In the embodiment shown in FIG. 2A, the body 26 is formed with a well-defined base portion 38. In other embodiments, the base portion could be configured to be less prominent a structure. In yet other embodiments, the base portion could be omitted altogether. In such embodiments, the arm portions would connect to each other.

With reference to FIGS. 2A and 2B, the elongate body 26 further includes a length $L_1$ measured between the mesial and distal faces 22 and 24 of the body 26, a width $W_1$ measured between the outer lateral surface 60 of the first arm portion 40 and the outer lateral surface 62 of the second arm portion 42, and a depth $H_1$ measured between the outer surface 64 of the base portion 38 and the outer surfaces 66 of the arm portions 40 and 42 disposed opposite the outer surface 64. In this embodiment, the body 26 is nearly as long as it is wide. In other embodiments, the body may be configured to have a length $L_1$ equal to, greater than or lesser than the width $W_1$.

Roughly midway between the third and fourth corners 34 and 36 and opposite the base portion 38, an arch wire entranceway 70 is formed within the body 26. The entranceway 70 runs the entire length of the body 26 and is generally funnel-shaped with a taper in the direction of the base portion 38 ultimately culminating in a throat 72. The funnel shape of the entranceway 70 is defined by a pair of opposed, first and second inclined body surfaces 74 and 76. The inclined body surfaces 74 and 76 are separated from each other by an angle $\theta_1$. In this embodiment, the angle $\theta_1$ measures approximately 60.8 degrees. It will be appreciated that in other embodiments, a different (greater or lesser) value for the angle $\theta_1$ may be used. In still other embodiments, the entranceway could be configured to have a different shape.

The size of the throat 72 corresponds to the distance $T_1$ between the inclined body surfaces 74 and 76 at the narrowest point of the entranceway 70. The distance $T_1$ is selected based on the size/diameter $D_1$ of the arch wire 50 (or the range of arch wires) to be gripped by the orthodontic gripping device 20. The distance $T_1$ must be large enough so that the arch wire 50 can be inserted into the arch wire receiving station 48 without the application of excessive force. But, care must be taken not to size the throat 72 so large as to permit the arch wire 50 to be released easily from the gripping jaw 52 through the throat 72. It has been found that sizing the distance $T_1$ to be within the range of between approximately 35% to approximately 40% of the diameter $D_1$ tends to meet the above-described design objectives. In other embodiments, the distance $T_1$ can be increased or decreased to suit a differently sized arch wire or a particular application.

The entranceway 70 (and more specifically, the throat 72) opens onto (or provides access to) the arch wire receiving station 48. In this embodiment, opposing, inner gripping surfaces 78 and 80 of the first and second jaw portions 44 and 46, respectively, are configured with a concavity or indentation 82 which impart a generally circular profile to the arch wire receiving station 48. Configured in this way, the profile of the arch wire receiving station 48 matches at least partially the cross-sectional (i.e. circular or substantially circular) shape of the arch wire 50.

This arrangement tends to maximize contact/engagement between the inner gripping surfaces 78 and 80 and the outer surface 84 of the arch wire 50 and tends to improve retention of the arch wire 50 within the arch wire receiving station 48 by ensuring that a proper distribution of gripping forces on the arch wire is achieved. By matching the geometry of the arch wire receiving station 48 to that of the arch wire 50, the risk of the arch wire being accidentally released from the gripping device in the event the arch wire or gripping device is exposed to a sudden impact, may be mitigated.

While matching the profile of the arch wire receiving station to that of the arch wire is generally preferred, it need not be the case in every application. In certain applications, the arch wire receiving station could be configured with a profile different from that of the arch wire.

Other modifications are possible. For instance, while in this embodiment the inner gripping surfaces 78 and 80 maintain the same arcuate profile throughout the length $L_1$ of body 26, in other embodiments the profiles of the inner gripping surfaces could be varied throughout the length of body. The inner gripping surfaces could feature an irregular surface profile. Instead of the inner gripping surfaces being smooth, they could be textured or roughened to enhance friction. Further still, the inner gripping surfaces could be coated with friction enhancing materials.

In this embodiment, by virtue of the circular profile of the arch wire receiving station 48, the centre point for the radius of curvature of the inner gripping surface 78 coincides with the centre point for the radius of curvature of the inner gripping surface 80, and both centre points lies on the longitudinal centreline $CL_1$.

The arch wire receiving station 48 has a diameter $D_2$ defined substantially by the opposing inner gripping surfaces 78 and 80. The diameter $D_2$ of the arch wire receiving station 48 is sized slightly smaller than the diameter $D_1$ of the arch wire 50. Preferably, the diameter $D_2$ is sized 20% smaller than the diameter $D_1$. In other embodiments, the sizing of diameter $D_2$ may differ.

Figure 4:
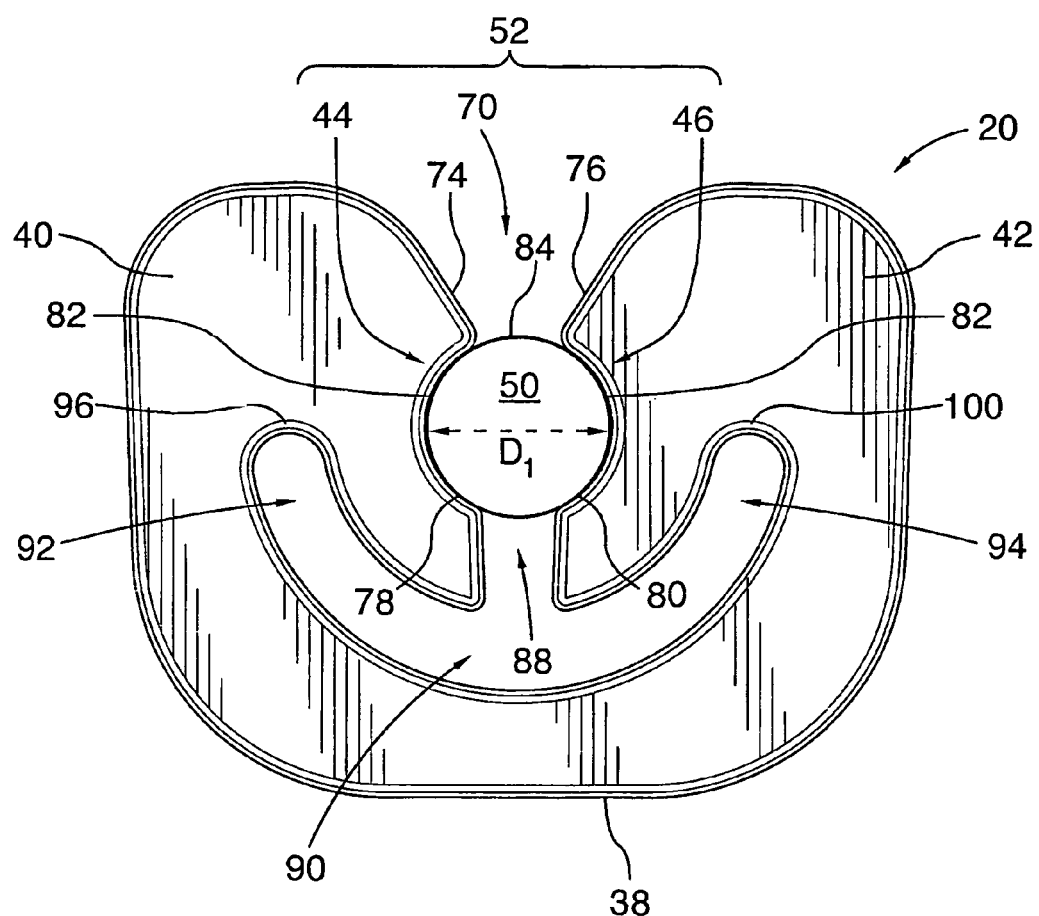
FIG. 4 is an end elevation (or mesial) view of the arch wire and orthodontic gripping device shown in FIG. 3.

During the attachment procedure, when the arch wire 50 is received in the arch wire receiving station 48, the first and second arm portions 40 and 42 deflect partially outwardly from each other to compensate for the fact that the diameter $D_2$ of the arch wire receiving station 48 is smaller than the diameter $D_1$ of the arch wire 50. Because the orthodontic gripping device 20 is made from a superelastic metal alloy, the arm portions 40 and 42 are resilient and biased to their original (undeflected) positions. As the arm portions 40 and 42 seek to return to their original positions, their inner gripping surfaces 78 and 80, which partially surround the arch wire 50, exert a clamping or gripping force on the outer surface 84 of the arch wire 50 (as best shown in FIG. 4). The application of this gripping force tends to hold the arch wire 50 tightly and tends to resist displacement (or arrest movement) of the gripping device 20 relative to the arch wire 50. It will thus be appreciated that the gripping jaw 52 derives its gripping force by putting to good advantage the special spring-back characteristics of the metal alloy to tightly clamp onto the arch wire 50. As a result, the gripping jaw 52 of the gripping device 20 tends to exert a greater gripping force on the arch wire than conventional arch wire stops and tends to offer better resistance against slippage.

When the gripping device 20 is used as an arch wire stop, movement of the arch wire relative to the gripping device will preferably be resisted in the mesial/distal direction. However, it should be noted that the gripping device would discourage movement in all directions and would tend to resist rotation about the arch wire.

Opposite the throat 72, the arch wire receiving station 48 opens onto a relatively narrow passageway 88. The passageway 88 extends toward the base portion 38 and communicates with an arcuate (generally U-shaped) cutout 90 having opposed first and second portion 92 and 94. The first portion 92 of the cutout 90 is defined between the first arm portion 40 and the base portion 38, and follows an arcuate path from the passageway 88 toward the third corner 34 of the body 26. The terminal end 96 of the first cutout portion 92 lines up roughly with the midpoint of the concavity 82 defined in the inner gripping surface 78 of the first gripping jaw portion 44. Configured in this way, the first cutout portion 92 defines a peninsular section 98 in the first gripping jaw portion 44.

In like fashion, the second portion 94 of the cutout 90 is defined between the second arm portion 42 and the base portion 38, and follows an arcuate path from the passageway 88 toward the fourth corner 36 of the body 26. The terminal end 100 of the second cutout portion 94 lines up roughly with the midpoint of the concavity 82 defined in the inner gripping surface 80 of the second gripping jaw portion 46. Configured in this way, the second cutout portion 94 defines a peninsular section 102 in the second gripping jaw portion 46. In other embodiments, cutout 90 could be configured differently.

The purpose of the cutout portions 92 and 94 is to permit the deflection of the gripping jaw portions 44 and 46 outwardly away from each other without the application of excessive force, when the arch wire 50 is being pushed through the throat 70 and into the arch wire receiving station 48. The cutout portions 92 and 94 also allow the peninsular sections 98 and 102 of the gripping jaw portions 44 and 46 to deflect toward the first and second corners 30 and 32, respectively, when the arch wire 50 is held in the arch wire receiving station 48 (as best shown in FIG. 4).

Figure 3:
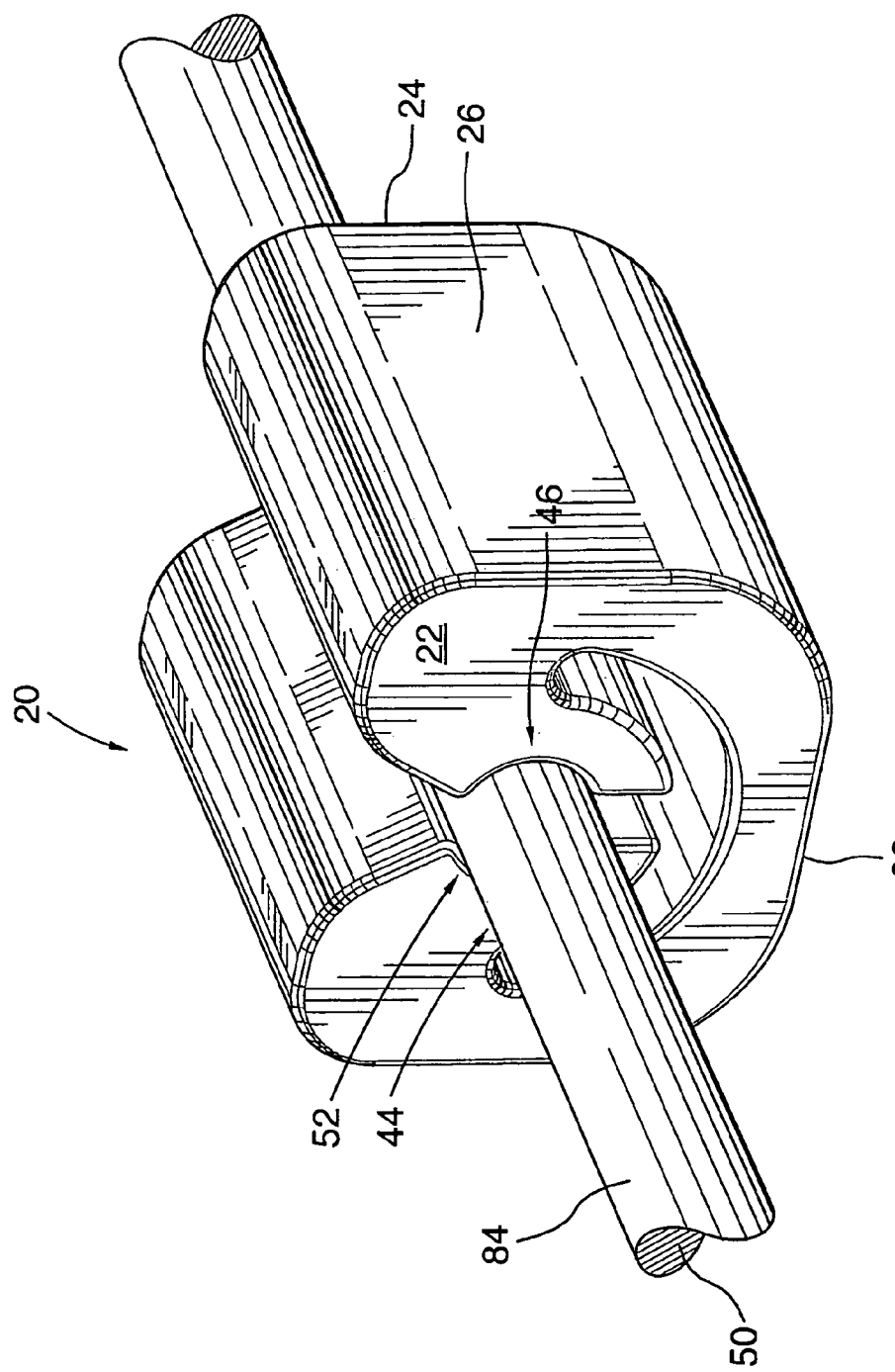
FIG. 3 is another perspective view showing the orthodontic gripping device of FIG. 1 attached to an arch wire of circular or substantially circular cross-section.

Turning now to FIGS. 3 and 4, a length of arch wire 50 is shown firmly retained by the gripping jaw 52 of the orthodontic gripping device 20. As previously mentioned, the arch wire 50 in this embodiment has a circular or substantially circular cross-section and a diameter $D_1$. It may be fabricated from linear elastic materials (e.g. stainless steel, cobalt chromium, titanium beta (III)), superelastic materials (including superelastic metal alloys, such as alloys of nickel titanium, nickel/titanium/copper, nickel/titanium/copper, nickel/titanium/copper/chromium), shape memory materials (including shape memory non-metallic materials, such as shape memory polymers; or shape memory metal alloys), or still other materials possessing superelastic or shape memory properties and suitable for use in orthodontic appliances.

For ease of illustration, the arch wire 50 is shown conceptually as being a single solid strand of wire. However, the arch wire 50 can take the form of a plurality of braided wire strands or helically wrapped wire strands. An example of such a helically wrapped arch wire is the arch wire manufactured and sold by Strite Industries Limited of Cambridge, Ontario, Canada under the brand name SPEED Supercable™. The arch wire used in conjunction with the gripping device 20 can have a core or alternatively, it may be coreless (i.e. it may have a hollow cylindrical centre). An example of such a coreless arch wire is an arch wire manufactured and sold by Strite Industries Limited under the brand name SPEED Tubular Supercable™. In a further alternative, the arch wire can take the form of a Hills Dual Geometry Wire, that is, a wire with a first section provided with a square cross-section and second section provided with a circular cross-section. In such a case, the orthodontic gripping device 20 could be used on the second section of circular cross-section.

Referring to FIGS. 6, 7, 8 and 9, there is shown an orthodontic tool in the nature of a pair of pliers 110 which may be used to attach the gripping device 20 to the arch wire 50. The pliers 110 have first and second arms 112 and 114 arranged in cross-wise fashion and pivotally connected to each other by a pivot connector 116. The first arm 112 includes a first end 118, an opposed second end 120, a first curved handle portion 122, a first beak portion 124 and a first transition portion 126 for joining the first handle portion 122 to the first beak portion 124. The first transition portion 126 is disposed at a location closer to the first end 118 than to the second end 120 and receives a portion of the pivot connector 116. The first handle portion 122 extends from the second end 120 to the first transition portion 126, while the first beak portion 124 runs from the first transition portion 126 to the first end 118. The first beak portion 124 has a generally tapering profile, but terminates with a first work tip 128 that extends on a slant relative to the longitudinal axis P of the pliers 110. In this embodiment, the angle α formed between the longitudinal axis P and the work tip 128 is 30 degrees (see FIG. 7). In other embodiments, a different angle α may be used.

Figure 6:
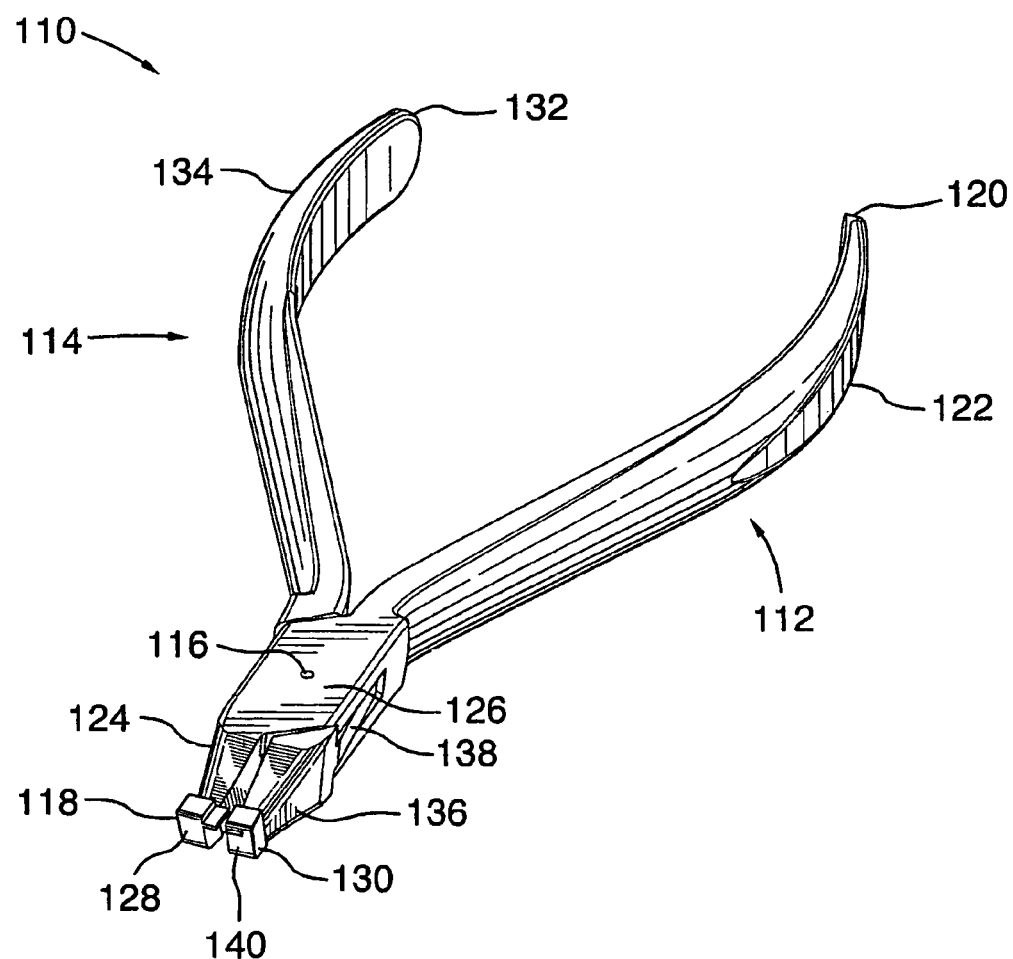
FIG. 6 is a perspective view of an orthodontic pair of pliers in accordance with an embodiment of the invention used to attach a gripping device onto an orthodontic arch wire.
Figure 7:
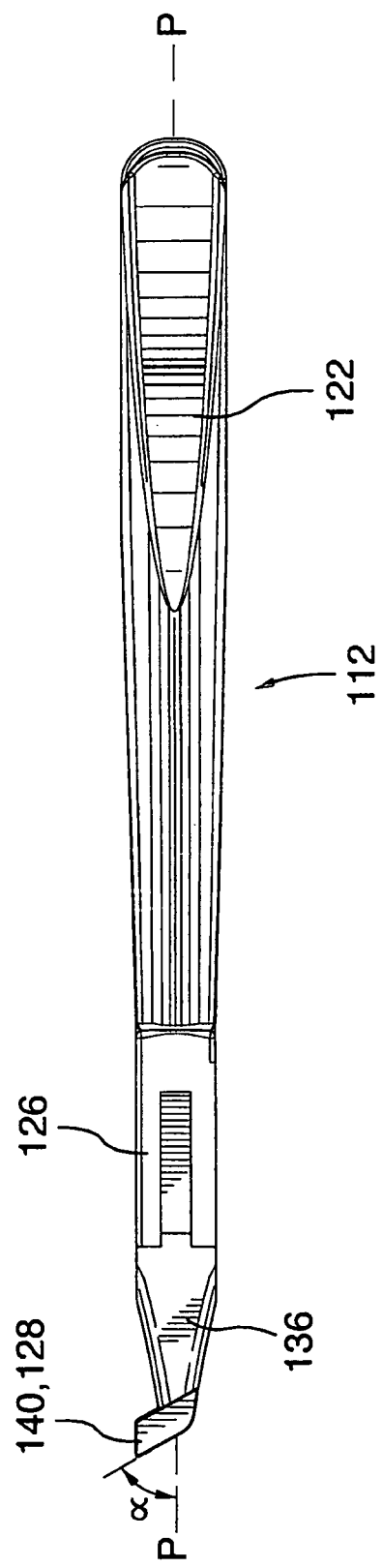
FIG. 7 is a side elevation view of the pliers shown in FIG. 6.

The second arm 114 is generally structurally similar to the first arm 112 in that it too has a first end 130, an opposed second end 132, a second curved handle portion 134, a second beak portion 136 and a second transition portion 138 joining the second handle portion 134 to the second beak portion 136. The second transition portion 138 is disposed at a location closer to the first end 130 than to the second end 132 and receives another portion of the pivot connector 116. Configured in this manner, the arms 112 and 114 are joined to each other by the pivot connector 116 at their respective transition portions 126 and 138. The second handle portion 134 extends from the second end 132 to the second transition portion 138, while the second beak portion 136 runs from the second transition portion 138 to the first end 130. The second beak portion 136 also has a generally tapering profile (as best shown in FIG. 6), but terminates with a second work tip 140 that extends on the same slant relative to the longitudinal axis P of the pliers 120 as work tip 128.

Figure 8:
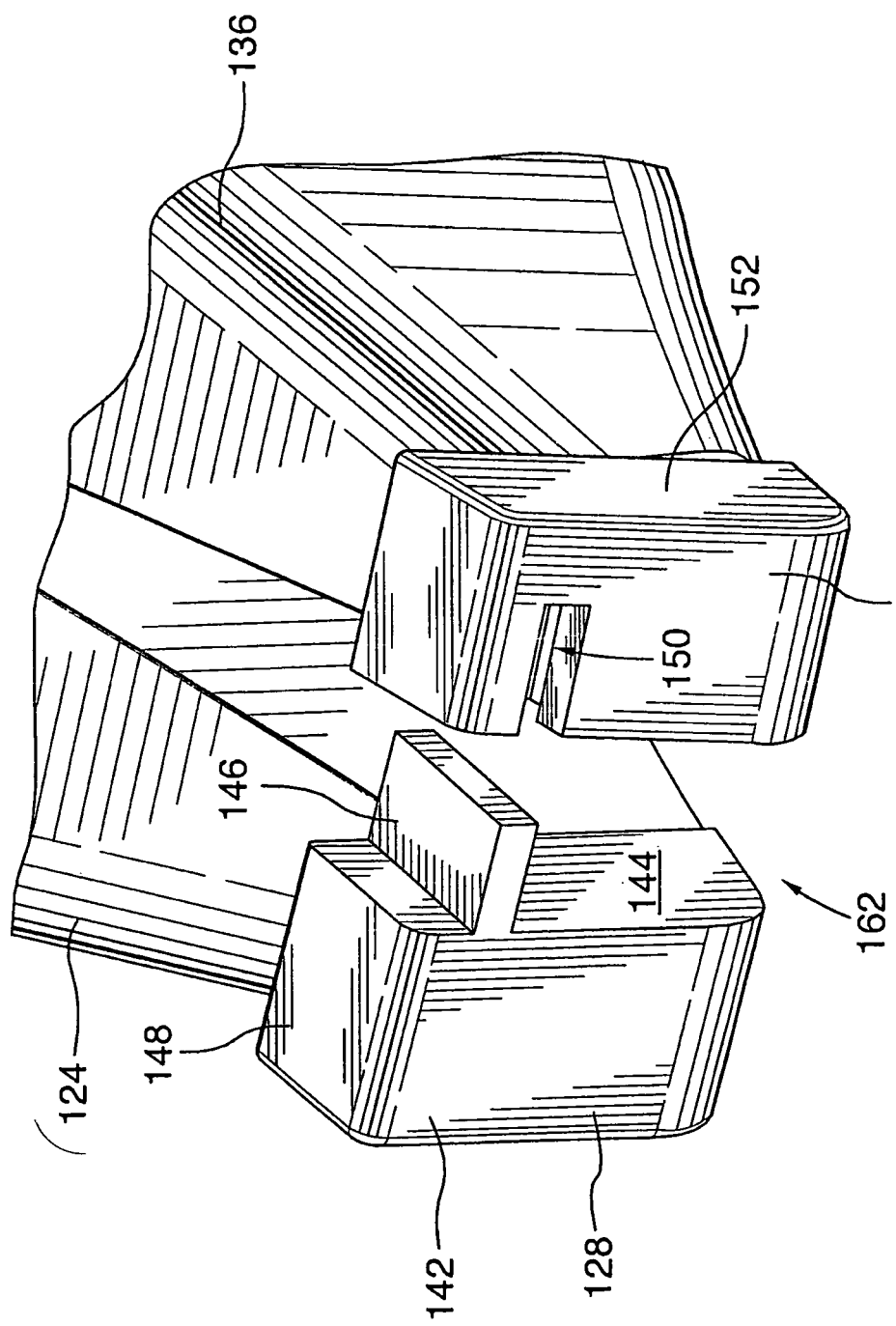
FIG. 8 is an enlarged perspective view of the first male and second female work tips of the pliers illustrated in FIG. 6, showing the pliers in an open setting with the male work tip spaced apart from the female work tip.
Figure 9:
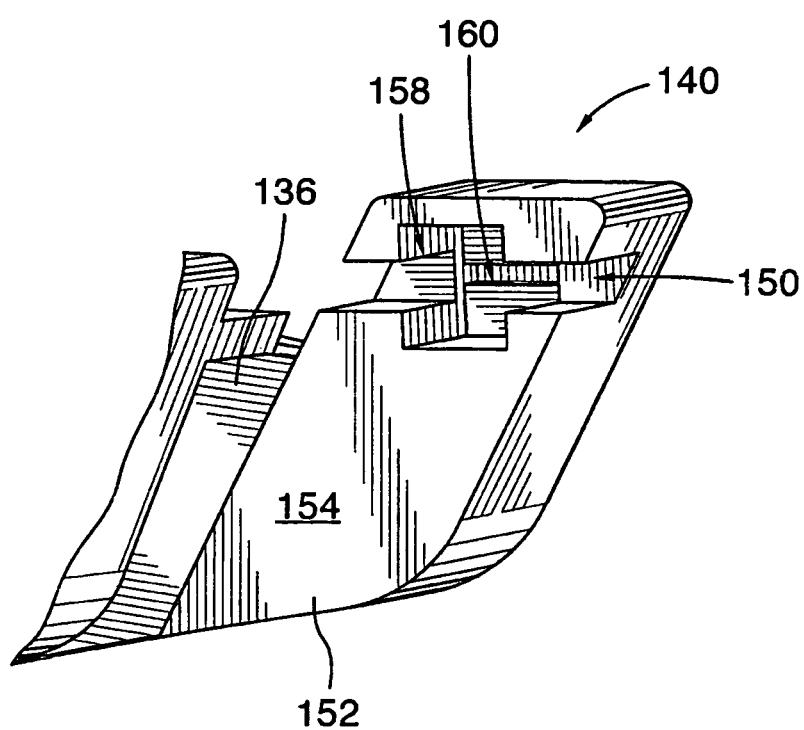
FIG. 9 is an enlarged, isolated perspective view of the female work tip shown in FIG. 8.

With reference to FIGS. 8 and 9, the first and second work tips 128 and 140 are now described in greater detail. The first work tip 128 has a generally block-like body 142 with an inner surface 144 oriented toward the second work tip 140. Projecting from the inner surface 144 in a generally perpendicular orientation is a flange 146. The flange 146 extends along the entire width of the body 142 and is carried close to the free end 148 of the work tip 128. As will be explained in greater detail below, the flange 146 is configured for registration with a transverse slot 150 defined within the second work tip 140. In an alternative embodiment, the flange could be configured differently.

Referring now specifically to FIG. 9, the second work tip 140 also includes a generally block-like body 152 with an inner surface 154 oriented toward the first work tip 128. The inner surface 154 is formed with the first, generally C-shaped, transverse slot 150 which spans the width of the body 152. The first transverse slot 150 is sized to accommodate a section of arch wire therein. In an alternative embodiment, the first transverse slot could be configured differently, for instance, it could be stepped so as to suit different sized arch wires.

A rectangular pocket or rebate 158 defined within the inner surface 154 partially overlies the transverse slot 150 with its short sides oriented generally parallel to the transverse slot 150. Advantageously, the rectangular rebate 158 is configured as a seat for holding an orthodontic gripping device, such as the gripping device 20, during attachment of the gripping device to the arch wire. The provision of this seat tends to minimize the incidents of accidental drop or loss of the gripping devices 20 and facilitates handling of the gripping devices, which because of their relatively small size can be unwieldy. In other embodiments, the handling of the gripping devices could be improved by incorporating a spring-loaded mechanism into the rectangular rebate to securely retain the gripping device. Alternatively, one of the second work tip and the gripping device could be coated with a tacky material which would assist in holding the gripping device on the pliers 110.

The body 152 is further provided with a second transverse slot 160 recessed from both the first transverse slot 150 and the rebate 158. The second transverse slot 160 is co-extensive with, and generally parallel to, the short sides of the rebate 158. The second transverse slot 160 provides a clearance to accommodate any protrusions extending from the base portion 38 which may be left over from the gripping device manufacturing process. Additional slots may be provided for the same purpose.

The arms 112 and 114 of the pliers 110 are movable relative to each other between a closed setting (not shown) and an open setting 162 (best shown in FIG. 8). In the closed setting, the flange 146 of the first male work tip 128 mates with the slot 150 of the second female work tip 140. In the open setting 162, a gap exists between the first and second work tips 128 and 140. To move the arms 112 and 114 from the open setting 162 to the closed setting, the user brings the first and second handle portions 122 and 134 toward each other. The arms 112 and 114 are made to pivot about the pivot connector 116 causing the first and second beak portions 124 and 136 to move toward each other thereby closing the gap between the first and second work tips 128 and 140. In an alternative embodiment, the pliers may be spring-loaded.

In a further embodiment, the arrangement of flange 146, first and second transverse slots 150 and 160 and rectangular rebate 158 could be oriented differently on the first and second work tips 128 and 140. For instance, in another embodiment, the arrangement could be rotated 90 degrees from the arrangement shown in FIG. 8.

An exemplary procedure for attaching the orthodontic gripping device 20 to the arch wire 50 using the orthodontic pliers 110 is now explained in greater detail. The orthodontist moves the arms 112 and 114 of the pliers 110 to the open setting 162 and orients the pliers such that the second arm 114 is disposed above the first arm 112. In this position, the rectangular rebate 158 defined in the second work tip 140 is accessible from the top. The orthodontist then places an orthodontic gripping device 20 into the second work tip 140 ensuring that the gripping device 20 is properly seated in the rectangular rebate 158 with its entranceway 70 oriented co-axially with the first transverse slot 150 and facing toward the first work tip 128. The proper placement of the gripping device 20 within the rebate 158 is facilitated by the generally rectangular shape of the gripping device body 26 as the body 26 tends not to rotate in the rebate 158. The gripping device 20 is now ready to be attached to the arch wire 50.

The orthodontist can attach the gripping device 20 on the arch wire 50 either while the arch wire 50 is fitted on the patient's dental arch or prior to the placement the arch wire 50 in the orthodontic appliances or brackets mounted to the patient's teeth. The orthodontist positions the pliers 110 over the section of arch wire to be retained within the gripping device 20 and aligns that section of arch wire 50 with the entranceway 70 (defined in the gripping device body 26) and the first transverse slot 150 of the second work tip 140. Preferably, if the gripping device 20 is being attached to an arch wire 50 already fitted on the patient's upper dental arch, the entranceway 70 would be directed toward the gingival. On the other hand, if the gripping device 20 is being attached to an arch wire 50 already fitted on the patient's lower dental arch, preferably, the entranceway 70 would be directed toward the occlusal. This further helps to avoid the gripping device 20 accidentally falling out of the pliers 110 during the attachment procedure. This need not be the case in every application. In other embodiments, it may be possible to orient the entranceway 70 differently, for example, toward the lingual or toward the labial.

Figure 10:
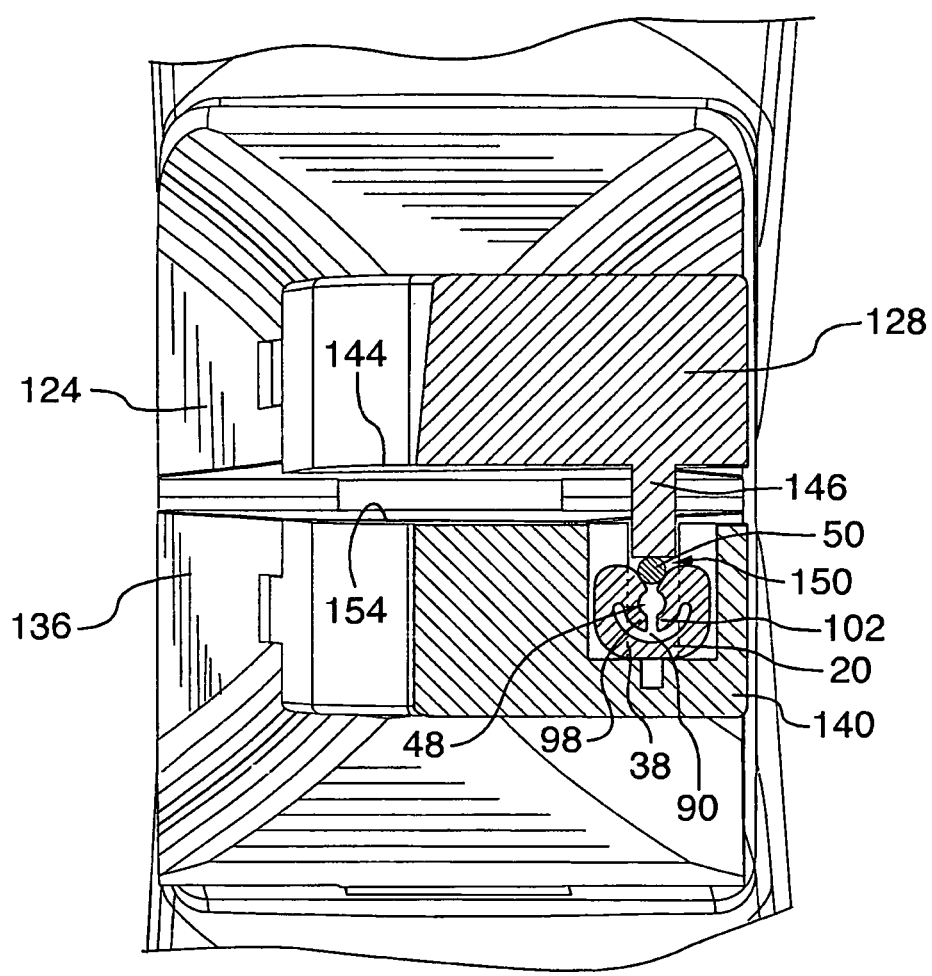
FIG. 10 is an end elevation view looking directly at the work tips of the pliers illustrated in FIG. 6 with a portion of the work tips removed for clarity, showing a gripping device of the type shown in FIG. 1 seated in a rebate defined in the female work tip of the pliers and the flange of the male work tip bearing against the outer surface of the arch wire.
Figure 11:
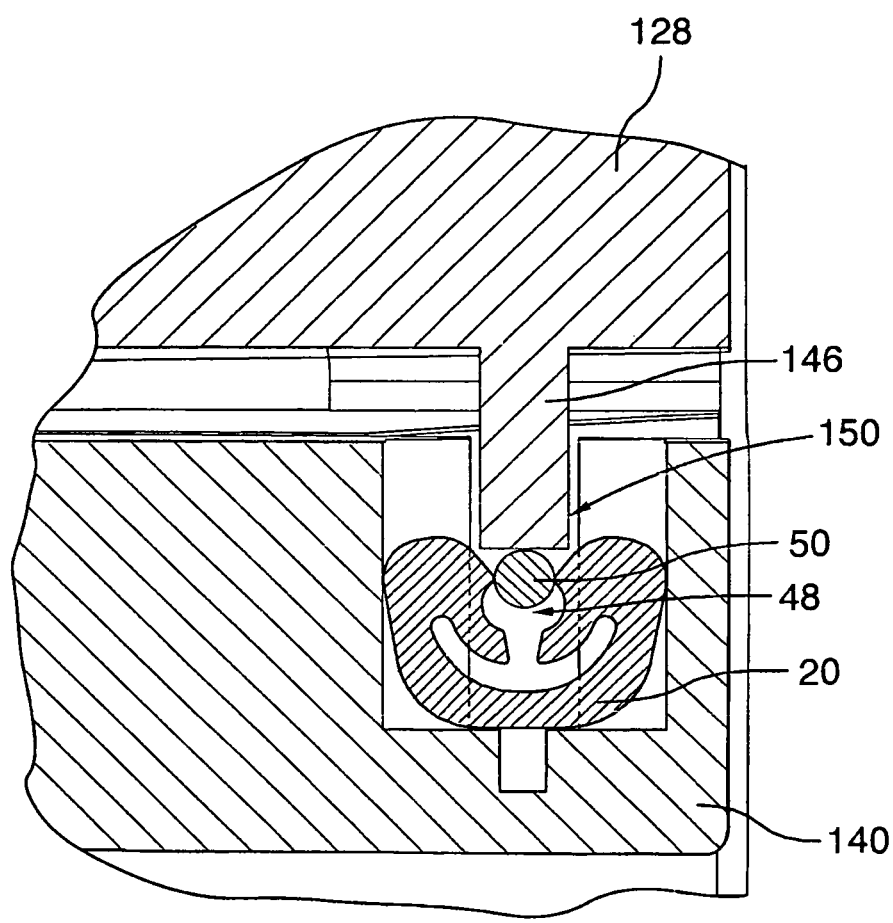
FIG. 11 is magnified elevation view of the work tips and gripping device illustrated in FIG. 10, with the arm portions of the gripping device shown deflecting outwardly from each other as the arch wire is admitted through the entranceway of the gripping device body.

The orthodontist then squeezes the handle portions 122 and 134 together thereby causing the flange portion 146 of the first work tip 128 to act upon the section of arch wire 50 to be retained (as best shown in FIG. 10). The flange portion 146 holds the arch wire 50 in place while the second work tip 140 causes the inclined body surfaces 74 and 76 to press against the arch wire. With the application of sufficient force, the arm portions 40 and 42 of the gripping device 20 will begin to deflect outwardly from each other and the throat 72 will widen to accommodate the arch wire 50 therein (see FIG. 11). Once the arch wire 50 has cleared the throat 72, the arm portions 40 and 42 will flex back toward each other in an attempt to return to their original (undeflected) positions. The inner gripping surfaces 78 and 80 of the first and second jaw portions 44 and 46 will come to bear on the outer surface 84 of the arch wire 50 and will hold the arch wire 50 tightly within the gripping device 20 thereby discouraging displacement of the gripping device 20 relative to the arch wire 50. With the gripping device 20 now attached to the arch wire 50, the orthodontist can move the arms 112 and 114 of the pliers 110 to the open setting 162 and release the gripping device 20 from the tool.

It should be appreciated that the orthodontic pliers 110 are specifically designed for the gripping device 20 and other similar gripping devices. Accordingly, while it is generally preferred for ease and convenience that the pliers 110 be used to attach a gripping device 20 or other similar gripping device to an arch wire, this need not be the case in every application. Other tools could be employed to attach the gripping device 20 or other like gripping device to the arch wire.

In the embodiment shown and described, the gripping device 20 is made of nickel titanium, a metal alloy that behaves in a linear superelastic mode. It should be appreciated that the exemplary attachment procedure described above applies specifically to gripping devices made of metal alloys behaving in a superelastic mode. Where the gripping device is a material that behaves in a shape memory mode, the attachment procedure would differ as explained below.

As an initial step, the gripping device would be cooled to a temperature within a temperature range that allows significant deformation of the memorized shape of the shape memory material (referred to herein as the shape reset temperature range). Cooling may be achieved by placing the gripping device in contact with cooling device or cooling media such as dry ice, right up to the time in time when it is to be deployed. A similarly cooled tool would be then inserted into the entranceway of the gripping device body to cause the arms of the gripping device to deflect outward. Because the temperature of the gripping device is below the shape recovery temperature range of shape memory material (i.e. the temperature range within which the shape memory material recovers its memorized shape), the arms would remain in their respective flexed or deflected positions even after removal of the tool, and the entranceway would remain open large enough to allow an arch wire of the desired diameter or width to pass through it and into the jaw of the gripping device.

Thereafter the orthodontist would rapidly place the gripping device in the desired position over an arch wire installed in a patient's oral cavity or exterior to the patient's oral cavity (in both cases such that the arch wire is located within the jaws of the gripping device). The gripping device would then be heated up to a temperature falling within the shape recovery temperature range. As the gripping device reaches a temperature within the shape recovery temperature range, the shape memory properties in the material cause the arms to move back toward each other in an attempt to return to their original (undeflected) positions. The inner gripping surfaces of the first and second jaw portions come to bear on the outer surface of the arch wire and hold the arch wire tightly within the gripping device thereby discouraging displacement of the gripping device relative the arch wire.

In certain embodiments, it may be desirable to have a shape recovery temperature range that is below the temperature of the human oral cavity (which is on average 36.8° C. but may vary among individuals and time of day). For example, where the shape memory material is nickel titanium, a shape recovery temperature range of between −15° C. and 5° C. could be employed. Of course, other temperature ranges could also be used. In this way, shape memory of the gripping device may be obtained simply by allowing the gripping device to warm back up to the natural temperature in the oral cavity. During this time, it is recommended that the gripping device be held in position at the desired point of attachment on the arch wire to avoid sliding or shifting of the gripping device along the arch wire. Given the relatively small size of the gripping device, this should take a very short time. In alternative embodiments, the shape recovery temperature range could encompass the temperature of a patient's oral cavity. In such embodiments, the shape recovery temperature range could be, for example, between 17° C. and 37° C.

In still other embodiments, the shape recovery temperature range could be higher than the temperature of the human oral cavity (but less than the temperature at which permanent plastic deformation occurs), for example, between 45° C. and 60° C. In such cases, a shape memory material having a shape reset temperature range that is below the temperature of the human oral cavity should be used, for example, between −36° C. and 0° C. Such a shape memory material should have a shape recovery temperature range sufficiently high such that the gripping device does not require constant cooling subsequent to being opened at low temperature. Moreover, the shape memory material would be selected to ensure that the gripping device retains sufficient gripping force when it cools to the temperature of the human oral cavity.

When the shape recovery temperature range is set higher than the temperature of the human oral cavity, the gripping device can be shipped and handled at ambient temperature and somewhat higher temperatures, including that of the human oral cavity, without causing the jaw of the gripping device to close. In such cases when attaching the gripping device to the arch wire, care should be taken to localize the application of the heat applied to the gripping device during the installation on an arch wire, and to take measures to prevent any thermal damage to the teeth or surrounding tissue near the point of installation.

Figure 5A:
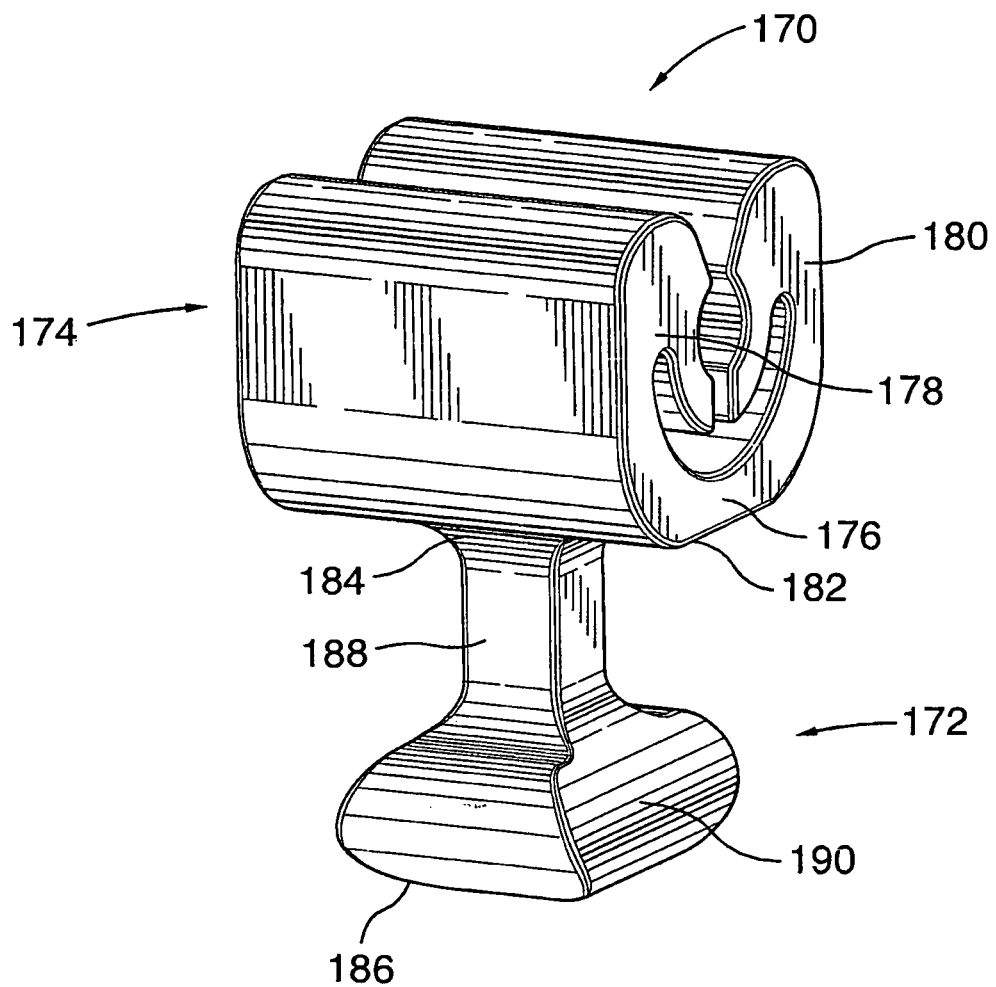
FIG. 5A is a perspective view of an orthodontic gripping device in accordance with a second embodiment of the invention showing an orthodontic gripping device provided with a hook.
Figure 5B:
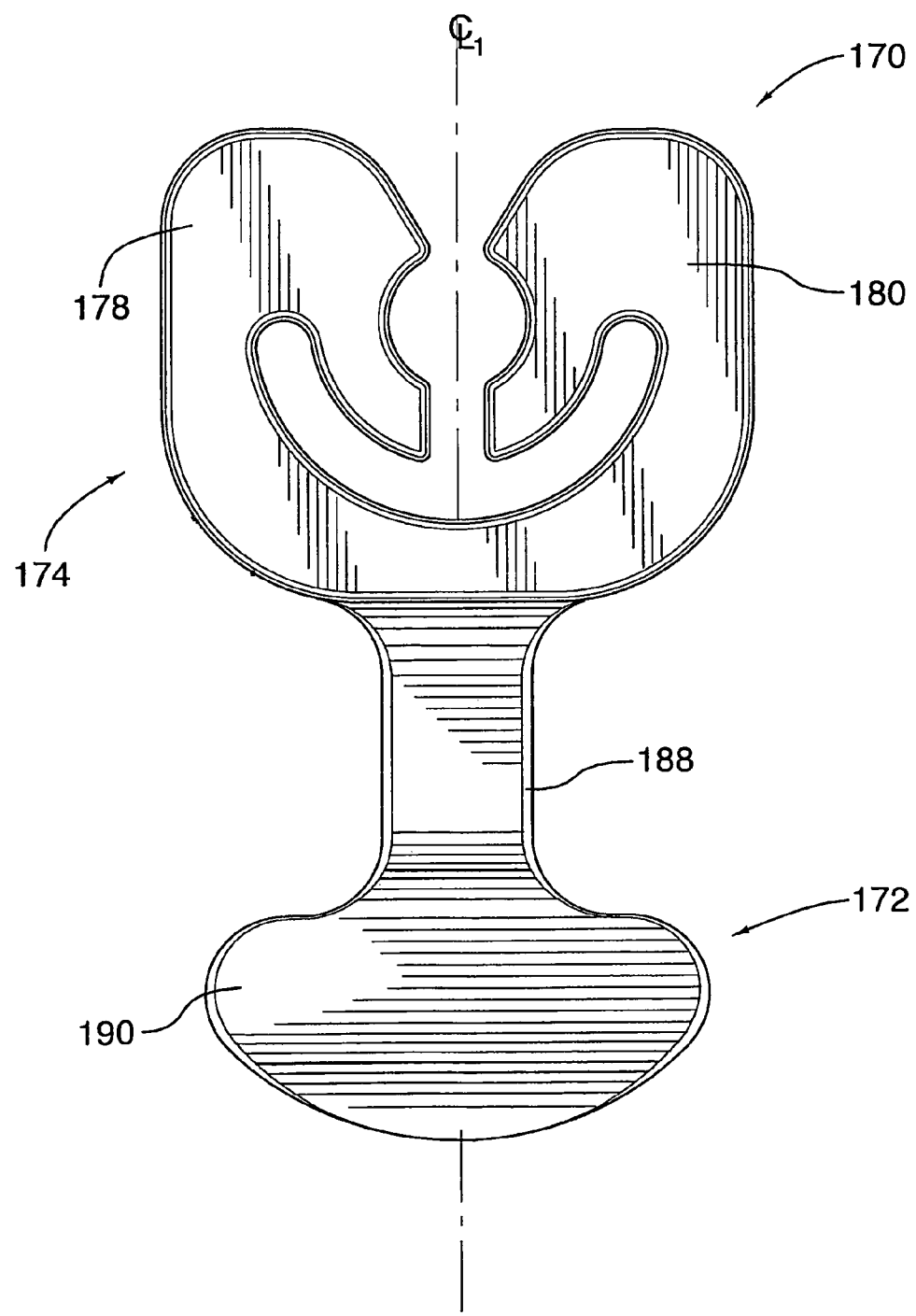
FIG. 5B is an end elevation (or mesial) view of the orthodontic gripping device shown in FIG. 5A.
Figure 5C:
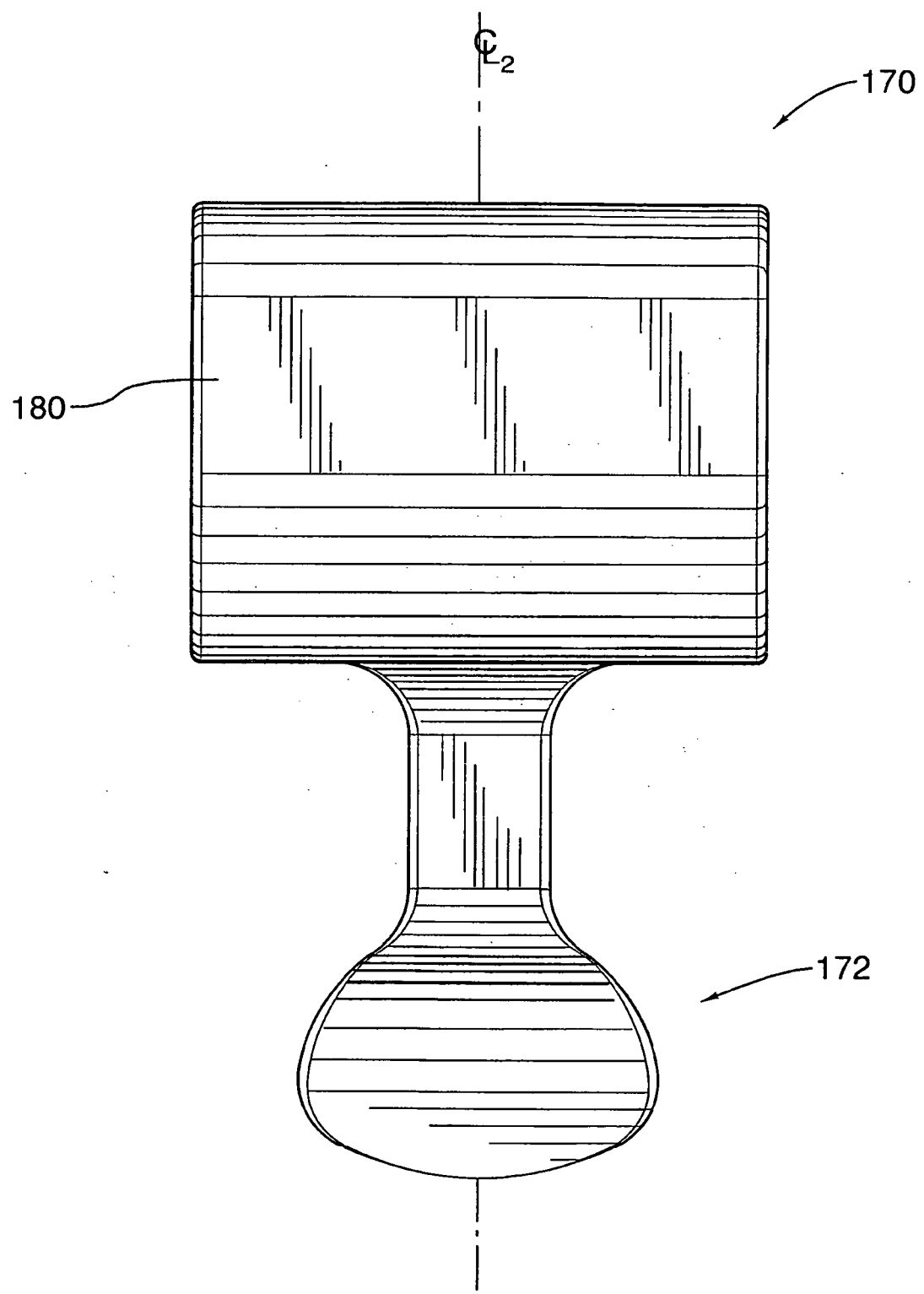
FIG. 5C is a side elevation view of the orthodontic gripping device shown in FIG. 5A.

Referring to FIGS. 5A, 5B and 5C, there is shown a second embodiment of an orthodontic gripping device constructed in accordance with the principles of the present invention. The gripping device in this embodiment is designated generally with reference numeral 170 and is similar in all material respects (i.e. functionality, configuration and construction) to the gripping device 20 shown in FIGS. 1 to 3, except that gripping device 170 is provided with a hook 172 which depends from the gripping device body 174.

The body 174 is similar to the body 26 in that it too includes a longitudinal centerline $CL_1$ (shown in FIG. 5B), a transverse centerline $CL_2$ (shown in FIG. 5C), a base portion 176 and a pair of opposed, spaced apart, first and second arm portions 178 and 180 connected to the base portion 176 and disposed on opposite sides of the centerline $CL_1$. The body 174 is symmetrical about the longitudinal centerline $CL_1$ such that the arm portions 178 and 180 are mirror images of each other. The body is also configured to be symmetrical about the transverse centerline $CL_2$.

However, in contrast to body 26, the body 174 has the hook 172 connected to the outer surface 182 of the base portion 176 and extending away from the first and second arm portions 178 and 180 along the centreline $CL_1$. In this embodiment, the hook 172 is integrally formed with the body 174. This need not be the case in every application. In other embodiments, the hook could be fabricated as a separate component and releasably or permanently fixed to the gripping device body.

Other modifications are also possible. For instance, the hook need not extend perpendicular to the base portion. It could extend from the base portion on a slant. While in this embodiment, the hook is centrally disposed on the base portion in alignment with the entranceway, in alternative embodiments, the hook could be positioned differently in relation to one of, or both, the base portion and the entranceway. In still other embodiments, the hook could be carried on one of the arm portions instead of on the base portion. The hook could extend from the arm portion in a perpendicular or slanted orientation. In embodiments where the hook is carried on one of the arm portions, it may be desirable to make the arm portion carrying the hook more robust (i.e. bigger and/or thicker) to better resist the forces applied to it by the hook. Conceivably, the hook could be mounted on any exterior surface of the gripping device body.

The hook 172 has a proximal end 184, a free end 186 and a stem 188 which extends between the proximal and free ends 184 and 186. At the proximal end 184, the stem 188 flares outwardly on all sides with smoothly radiused surfaces. At a location closer to the free end 186 than to the proximal end 184, the stem 188 again flares outwardly in all sides with smoothly radiused surfaces only to taper inwardly again a short distance later. This configuration defines the bulbous tip 190 of the hook 172. In other embodiments, the hook 172 could be shaped differently.

In the embodiment shown in FIGS. 5A, 5B and 5C, the gripping device 170 is shown provided with a hook 172. In other embodiments, the gripping device could be outfitted with accessories other than a hook. For instance, in an alternative embodiment, an auxiliary slot or an eyelet could be formed in the body of the gripping device.

During orthodontic treatment, the gripping device 170 may serve a dual purpose—it can arrest movement of the arch wire in the mesial/distal direction while serving as an anchoring point for tying orthodontic elastic/elastomeric bands or ligature ties (metal or elastomeric) or traction force springs.

The gripping device 170 may be attached to the arch wire 50 in much the same manner as the gripping device 20. However, the pliers 110 would have to be modified to provide a larger clearance than that currently provided by second transverse rebate 160 in order to accommodate the hook 172.

In the embodiments shown in FIGS. 1 through 5C, the gripping devices 20 and 170 are configured to receive and clamp tightly onto an arch wire of circular cross-section. However, this need not be the case in every application. In a third embodiment illustrated in FIGS. 12 to 17, there is shown an orthodontic gripping device 200 which is configured for use with an arch wire 202 of substantially rectangular cross-section.

Figure 12:
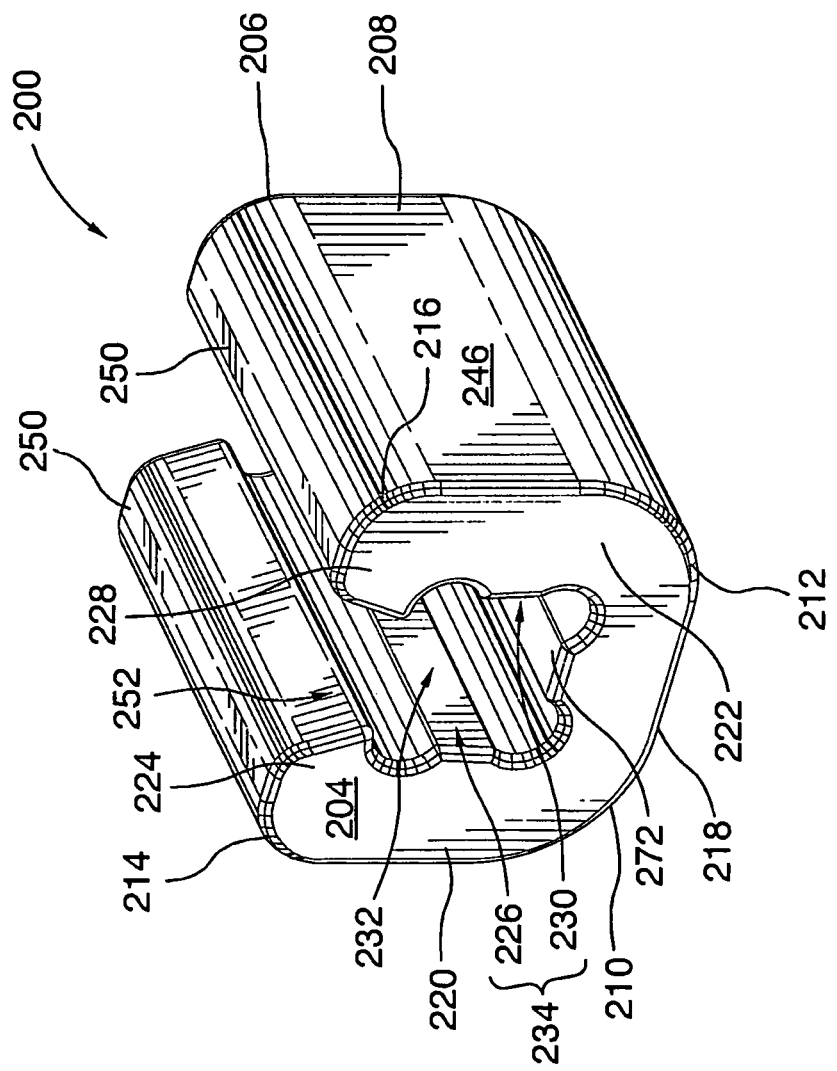
FIG. 12 is a perspective view of an orthodontic gripping device in accordance with a third embodiment of the invention.
Figure 13A:
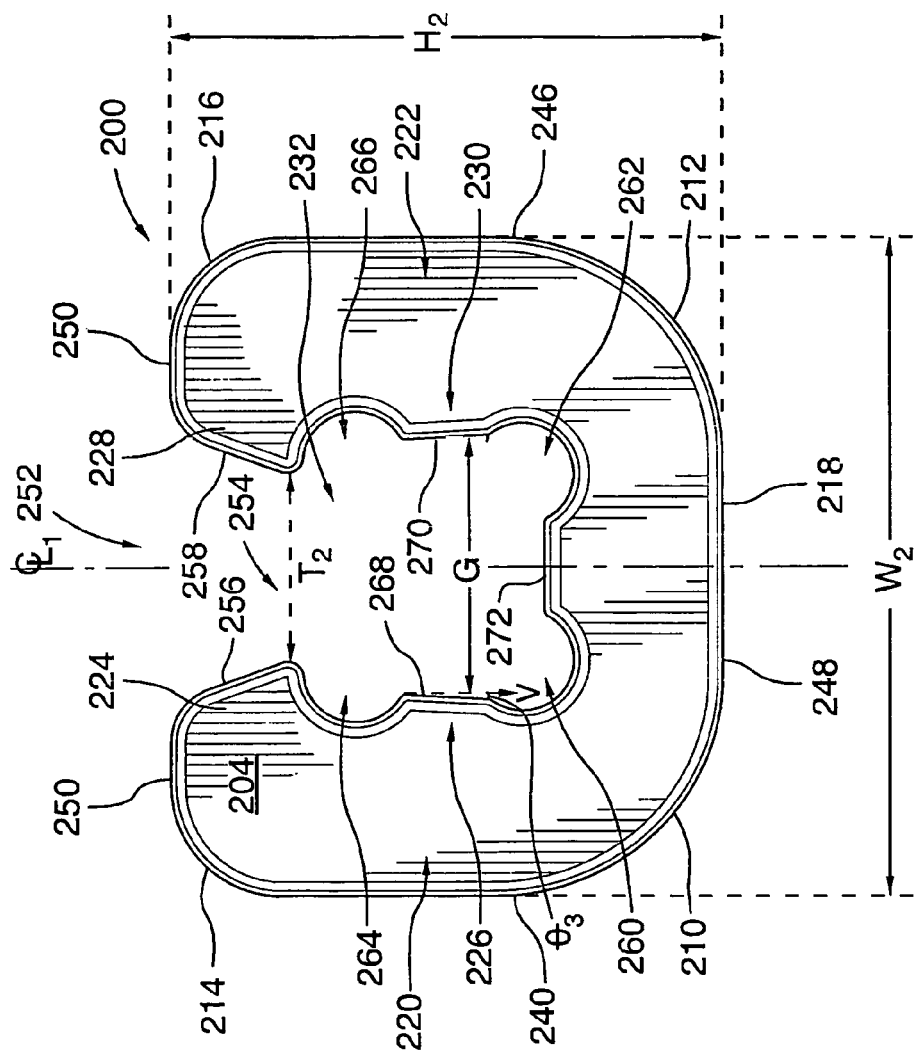
FIG. 13A is an end elevation (or mesial) view of the orthodontic gripping device shown in FIG. 12.
Figure 13B:
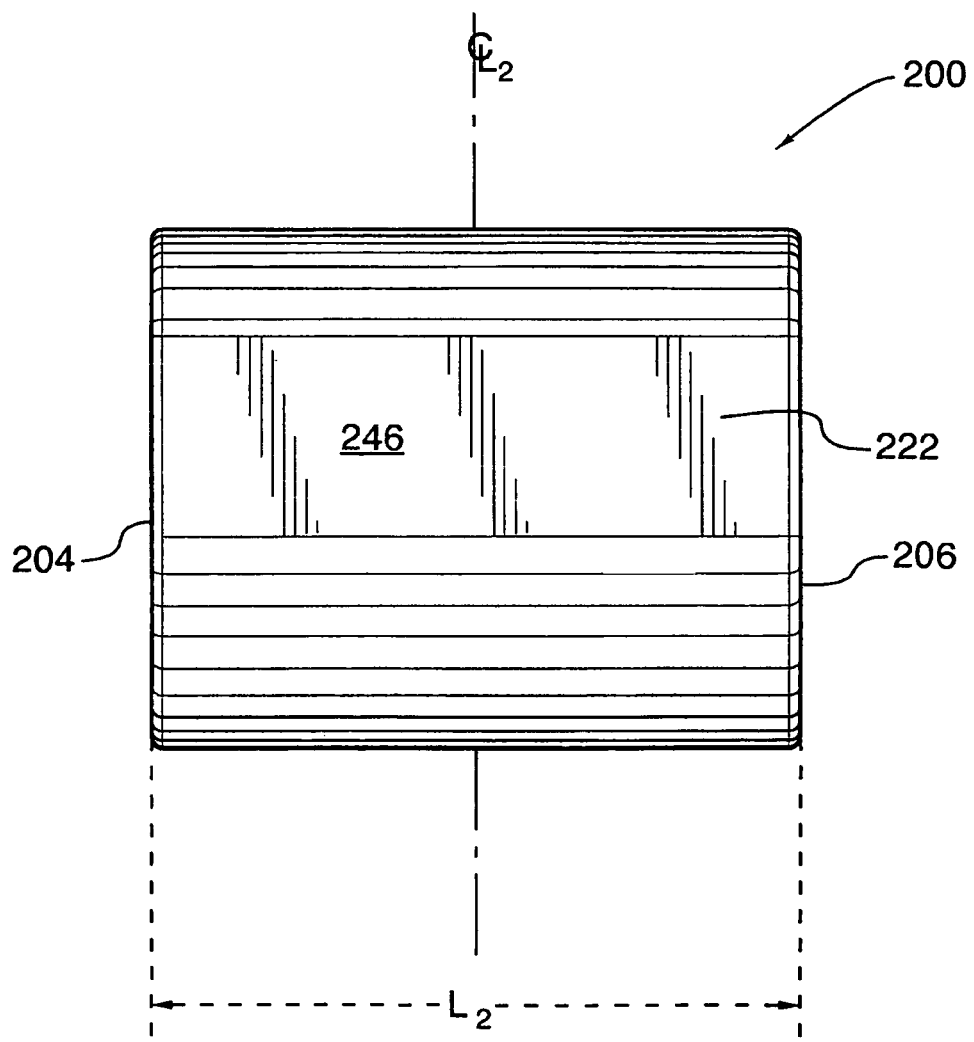
FIG. 13B is a side elevation view of the orthodontic gripping device shown in FIG. 12.

Referring to FIGS. 12, 13A and 13B, the gripping device 200 is generally similar to gripping device 20 described above in that it too has a mesial face 204 and a distal face 206 and an elongate body 208 extending between the mesial and distal faces 204 and 206. In this embodiment, the body 208 is of unitary (one-piece or monolithic) construction fabricated from a superelastic material. Preferably, such material is a superelastic metal alloy. Most preferably, the superelastic metal alloy is nickel titanium, or nickel titanium and other alloying elements (e.g. chromium (Cr), iron (Fe), vanadium (V), aluminium (Al), copper (Cu), cobalt (Co)), such as nickel/titanium/copper or nickel/titanium/copper/chromium. Preferably, the nickel titanium, or nickel titanium and other alloying elements, is cold worked. Although, cold worked and aged nickel titanium, or cold worked and aged nickel titanium and other alloying elements, could also be used. In this embodiment, the gripping device 200 is made of cold worked nickel titanium.

However, it should be appreciated that the gripping device could also be made from other materials suitable for use in orthodontic appliances and exhibiting spring-back properties similar to those exhibited by superelastic materials. For example, a gripping device fabricated from cold worked titanium beta III or solution heat treated and aged titanium beta III (a titanium molybdenum alloy) has been found to have superior gripping strength. Still other materials may be selected based on their ability to resist permanent deformation and/or mechanical failure when the gripping device is flexed during its engagement with the arch-wire, while at the same time possessing sufficient material stiffness, such that the gripping device exhibits sufficient spring-back to hold the arch-wire firmly in place once the gripping device is fully engaged with the arch wire.

In still other embodiments, the gripping device could be made of a shape memory material, such a shape memory metal alloy. Although, conceivably, a non-metallic material (such as a polymer) possessing shape memory properties could also be used.

Like body 26 of gripping device 20, the body 208 has a vaguely rectangular shape or profile when seen in a mesial view such as shown in FIG. 13A. The shape of the body 208 is defined substantially by four smoothly radiused corners—first corner 210, second corner 212, third corner 214 and fourth corner 216. The corners 210, 212, 214 and 216 are rounded so as to avoid the formation of abrupt projecting edges which could otherwise irritate the soft tissue in the patient's mouth and cause discomfort when the orthodontic gripping device 200 is deployed in the patient's mouth.

The body 208 includes a longitudinal centreline $CL_1$ (shown in FIG. 13A), a transverse centerline $CL_2$ (shown in FIG. 13B), a base portion 218 and a pair of opposed, spaced apart, first and second arm portions 220 and 222 connected to the base portion 218 and disposed on opposite sides of the longitudinal centerline $CL_1$. The body 208 is symmetrical about the longitudinal centerline $CL_1$ such that the arm portions 220 and 222 are mirror images of each other. The body 208 is also configured to be symmetrical about a transverse centerline $CL_2$. In other embodiments, the body could be configured asymmetrically about one or both the longitudinal centerline $CL_1$ and the transverse centerline $CL_2$.

The first arm portion 220 joins the base portion 218 at the first corner 210, while the second arm portion 222 attaches to the base portion 218 at the second corner 212. Each arm portion 220, 222 extends away from corner 210, 212, respectively, in a direction generally perpendicular to the base portion 218. At the third corner 214, the first arm portion 220 turns inwardly toward the second arm portion 222 and ultimately, terminates with a first stub-like projection 224. The section of the first arm portion 220 which runs between the first stub-like projection 224 and the base portion 218 defines a first jaw portion 226. Similarly, the second arm portion 222 turns inwardly toward the first arm portion 220 at the fourth corner 216 to terminate with a second stub like projection 228. The section of the second arm portion 222 which runs between the second stub-like projection 228 and the base portion 218 defines a second jaw portion 230.

The first and second jaw portions 226 and 230 are arranged opposite one another and separated by a relatively small gap which defines an arch wire receiving slot or station 232 for captively engaging (securely retaining) the arch wire 202 therein. Configured in this manner, the first and second jaw portions 226 and 230 together define the gripping jaw 234 of the orthodontic gripping device 200 (as best shown in FIG. 12).

With reference to FIGS. 12, 13A and 13B, the elongate body 208 further includes a length $L_2$ measured between the mesial and distal faces 204 and 206, a width $W_2$ measured between the outer lateral surface 240 of the first arm portion 220 and the outer lateral surface 246 of the second arm portion 222, and a depth $H_2$ measured between the outer surface 248 of the base portion 218 and the outer surfaces 250 of the arm portions 220 and 222 disposed opposite to the outer surface 248. In this embodiment, the body 208 is nearly as long as it is wide. In other embodiments, the body may be configured to have a length $L_2$ equal to, lesser than or greater than the width $W_2$.

Roughly midway between the third and fourth corners 214 and 216 and opposite the base portion 218, an arch wire entranceway 252 is formed within the body 208. The entranceway 252 runs the entire length of the elongate body 208 and is generally funnel-shaped with a taper in the direction of the base portion 218 ultimately culminating in a throat 254. The funnel shape of the entranceway 252 is defined by a first inclined surface 256 presented by the first stub-like projection 224 and a second inclined surface 258 presented by the second stub-like projection 228. The inclined body surfaces 256 and 258 are separated from each other by an angle $\theta_2$ (not represented in the figures). In this embodiment, the angle $\theta_2$ measures approximately 24 degrees. It will be appreciated that in other embodiments, a different (greater or lesser) value for the angle $\theta_2$ may be used.

The size of the throat 254 corresponds to the distance $T_2$ between the inclined surfaces 256 and 258 at the narrowest point of the entranceway 252. The distance $T_2$ is selected based on the size (i.e. width $W_3$) of the arch wire 202 (or the range of arch wires) to be retained by the orthodontic gripping device 200. The distance $T_2$ must be large enough so that the gripping device 200 can be fitted onto the arch wire 202 without the application of excessive force. But, care must be taken not to size the throat 254 so large as to permit the arch wire 202 to be released easily from the gripping jaw 234 through the throat 254. It has been found that sizing the distance $T_2$ to be within the range of between approximately 65% to approximately 70% of the width $W_3$ tends to meet the above-described design objectives. In other embodiments, the distance $T_2$ can be increased or decreased to suit a differently sized arch wire or a particular application.

The entranceway 252 (and more specifically, the throat 254) opens onto (or provides access to) the arch wire receiving station 232. In this embodiment, the arch wire receiving station 232 is shaped generally like a quatrefoil (but for the missing fourth side corresponding to the location of the throat 254). Defining this quatrefoil-like shape are four rounded undercuts or clearances formed in the body 208—a first undercut 260 located adjacent the first corner 210, a second undercut 262 located adjacent the second corner 212, a third undercut 264 located adjacent the third corner 214 and a fourth undercut 266 located adjacent the fourth corner 216—and three inner surfaces—a pair of opposing, inner gripping surfaces 268 and 270 of the first and second jaw portions 226 and 230 and an inner surface 272 of the base portion 218 as best shown in FIG. 13A. The undercuts 260, 262, 264 and 266 are provided to accommodate the radiused corners 274, 276, 278 and 280 of the arch wire 202. While not generally preferred, in alternative embodiments, the arch wire receiving station could be configured without any undercuts. For example, the arch wire receiving station could have a generally square or rectangular profile.

The inner surface 272 defines a seat for supporting side 288 of the arch wire 202. It extends between the first and second undercuts 260 and 262 and is substantially parallel with the outer surface 248 of the base portion 218.

The inner gripping surface 268 of the first jaw portion 226 extends between the first and third undercuts 260 and 264, while the inner gripping surface 270 of the second jaw portion 230 runs between the second and fourth undercuts 262 and 266. Each of the inner gripping surfaces 268 and 270 has a slightly skewed orientation relative to the longitudinal centerline $CL_1$. More specifically, as the inner gripping surface 268 extends from the first undercut 260 to the third undercut 264 it tapers inwardly toward the opposed gripping surface 270. Similarly, the inner gripping surface 270 tapers inwardly toward the gripping surface 268 in the direction of the fourth undercut 266. Stated differently, the first and second inner gripping surfaces 268 and 270 can be said to converge toward each other in the direction of the entranceway 252. In this embodiment, the angle of taper $\theta_3$ for each gripping surface 268, 270 (as measured between a vertical axis V (generally parallel to the longitudinal centerline $CL_1$) and each inner gripping surface 268, 270, as the case may be) is 3 degrees.

This taper tends to encourage better contact/engagement between the gripping surfaces 268 and 270 and the lateral sides 284 and 286 of the arch wire 202 when the arch wire 202 is received within the arch wire receiving station 232 and the arm portions 220 and 222 are partially deflected. This tends to improve retention of the arch wire 202 within the arch wire receiving station 232 by ensuring that a proper distribution of gripping forces on the arch wire is achieved. In this way, the risk of the arch wire being accidentally released from the gripping device in the event the arch wire or gripping device is exposed to a sudden impact, may be mitigated.

In other embodiments, a different (i.e. greater or lesser) angle of taper $\theta_3$ for both inner gripping surfaces may be used. In a further alternative, these inner gripping surfaces could be provided with no taper whatsoever. In such an embodiment, the first and second inner gripping surfaces would be oriented substantially parallel to the longitudinal centerline $CL_1$.

Preferably, the width of the arch wire receiving station 232 at its narrowest point (as measured between the inner gripping surfaces 268 and 270 at the location where these surfaces meet with the third undercut 264 and the fourth undercut 266, respectively) is at least 10% smaller than the width $W_3$ of the arch wire 202. However, in other embodiments, the width of the arch wire receiving station could be sized differently.

Other modifications are possible. For instance, while in this embodiment the inner gripping surfaces 268 and 270 maintain the same profile throughout the length $L_2$ of body 208, in other embodiments the profiles of the inner gripping surfaces could be varied throughout the length of body. The inner gripping surfaces could be irregular. Instead of the inner gripping surfaces being smooth, they could be textured or roughened to enhance friction. Further still, the inner gripping surfaces could be coated with friction enhancing materials.

In this embodiment, because the inner gripping surfaces 268 and 270 have a skewed orientation, the gap or distance G between the surfaces 268 and 270 is not constant. The gap G at the narrowest point between the inner gripping surfaces 268 and 270 (i.e. where the gripping surfaces 268 meets the third undercut 264 and the gripping surface 270 meets the fourth undercut 266) is sized smaller than the width $W_3$. In embodiments where the inner gripping surfaces are oriented substantially parallel to the longitudinal centerline $CL_1$, the gap G as measured at any location between the inner gripping surfaces will also be sized smaller that the width $W_3$.

Figure 15:
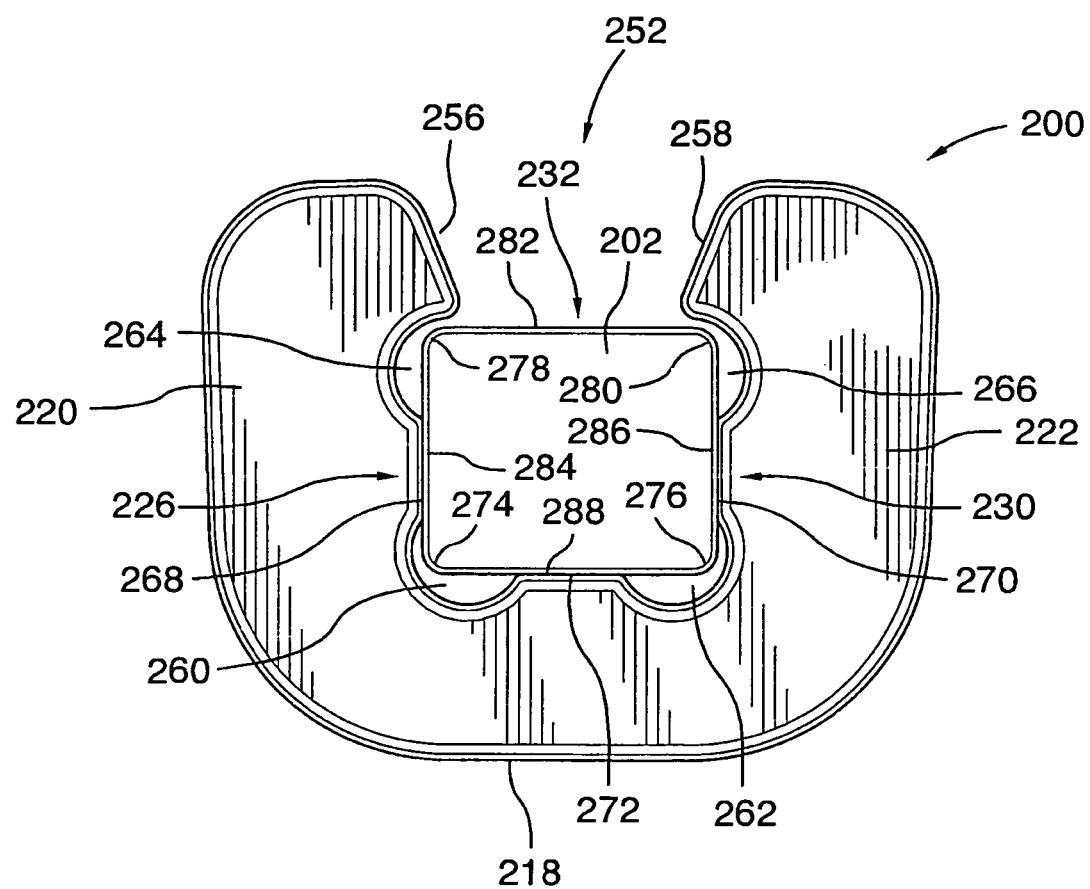
FIG. 15 is an end elevation (or mesial) view of the arch wire and orthodontic gripping device shown in FIG. 14.

During the attachment procedure, when the arch wire 202 is received in the arch wire receiving station 232, the first and second arm portions 220 and 222 deflect partially outwardly from each other to compensate for the fact that the gap G measured at the narrowest point between the inner gripping surfaces 268 and 270 is smaller than the width $W_3$ of the arch wire 202. Because the orthodontic gripping device 200 is made from a superelastic metal alloy, the arm portions 220 and 222 are resilient and biased to their original (undeflected) positions. As the arm portions 220 and 222 seek to return to their original positions, their inner gripping surfaces 268 and 270 apply a clamping or gripping force on the lateral sides 284 and 286 of the arch wire 202 (as best shown in FIG. 15). The application of this gripping force tends to hold the arch wire 202 tightly and tends to resist displacement (or arrest movement) of the gripping device 200 relative to the arch wire 202. It will thus be appreciated that the gripping jaw 234 derives its gripping force by putting to good advantage the special spring-back characteristics of the metal alloy to clamp tightly onto the arch wire 202. As a result, the gripping jaw 234 of the gripping device 200 tends to exert a greater gripping force on the arch wire than conventional arch wire stops and tends to offer better resistance against slippage.

When the gripping device 200 is used as an arch wire stop, displacement will preferably be resisted in the mesial/distal direction. However, it should be noted that the gripping device would also discourage movement in all directions and also tends to resist rotation about the arch wire.

Figure 14:
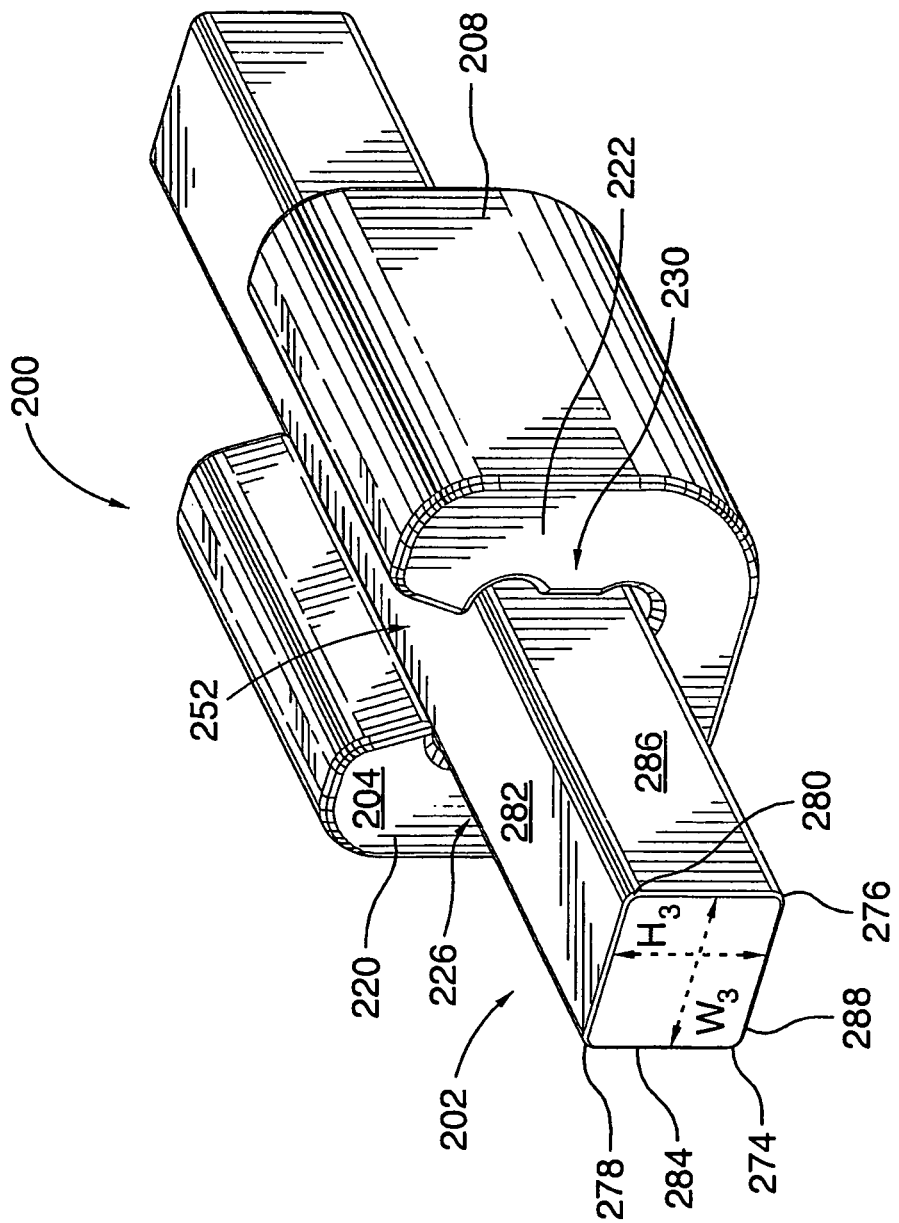
FIG. 14 is another perspective view showing the orthodontic gripping device of FIG. 12 attached to an arch wire with a substantially rectangular cross-section.

Turning now to FIGS. 14 and 15, a length of arch wire 202 is shown firmly retained by the gripping jaw 234 of the orthodontic gripping device 200. The arch wire 202 in this embodiment has a rectangular or substantially rectangular cross-section defined by lateral sides 284 and 286 (i.e. the short sides) extending between rounded corners 274 and 278, and rounded corners 276 and 280, respectively, and opposed sides 282 and 288 (i.e. the long sides) running between rounded corners 278 and 280, and rounded corners 274 and 276. The width $W_3$ of the arch wire 202 is defined as the distance between the lateral sides 284 and 286, while the depth $H_3$ of the arch wire 202 is defined by the distance between the sides 282 and 288.

For ease of illustration, the arch wire 202 is shown conceptually as being a single solid strand of wire. However, the arch wire 202 can take the form of a plurality of braided wire strands or helically wrapped wire strands. This multi-stranded arch wire may be formed (e.g. by rolling) to have a generally rectangular cross-section with rounded corners and may possess a core or be coreless.

Attachment of the orthodontic gripping device 200 to the arch wire 202 is similar to the attachment of the gripping device 20 to arch wire 50 described above. The orthodontist moves the arms 112 and 114 of the pliers 110 to the open setting 162 and orients the pliers such that second arm 114 is disposed above the first arm 112. In this position, the rectangular rebate 158 defined in the second work tip 140 is accessible from the top. The orthodontist then places an orthodontic gripping device 200 into the second work tip 140 ensuring that the gripping device 200 is properly seated in the rectangular rebate 158 with its entranceway 252 oriented parallel to the first transverse slot 150. The gripping device 200 is now ready to be attached to the arch wire 202.

The orthodontist can attach the gripping device 200 on the arch wire 202 either while the arch wire 202 is fitted on the patient's dental arch or prior to the placement of the arch wire 202 in the orthodontic appliances or brackets mounted to the patient's teeth. The orthodontist positions the pliers 110 over the section of arch wire to be retained within the gripping device 200 and aligns that section of arch wire with the entranceway 252 (defined in the gripping device body 208) and the first transverse slot 150 of the second work tip 140. Preferably, if the gripping device 200 is being attached to an arch wire 202 already fitted on the patient's upper dental arch, the entranceway 252 will be directed toward the gingival. On the other hand, if the gripping device 200 is being attached to an arch wire 202 already fitted on the patient's lower dental arch, preferably, the entranceway 252 will be directed toward the occlusal. This further helps prevent the gripping device 200 from accidentally falling out of the pliers 110 during the attachment procedure. This need not be the case in every application. In other embodiments, it may be possible to orient the entranceway 252 differently, for example, toward the lingual or toward the labial.

Figure 16:
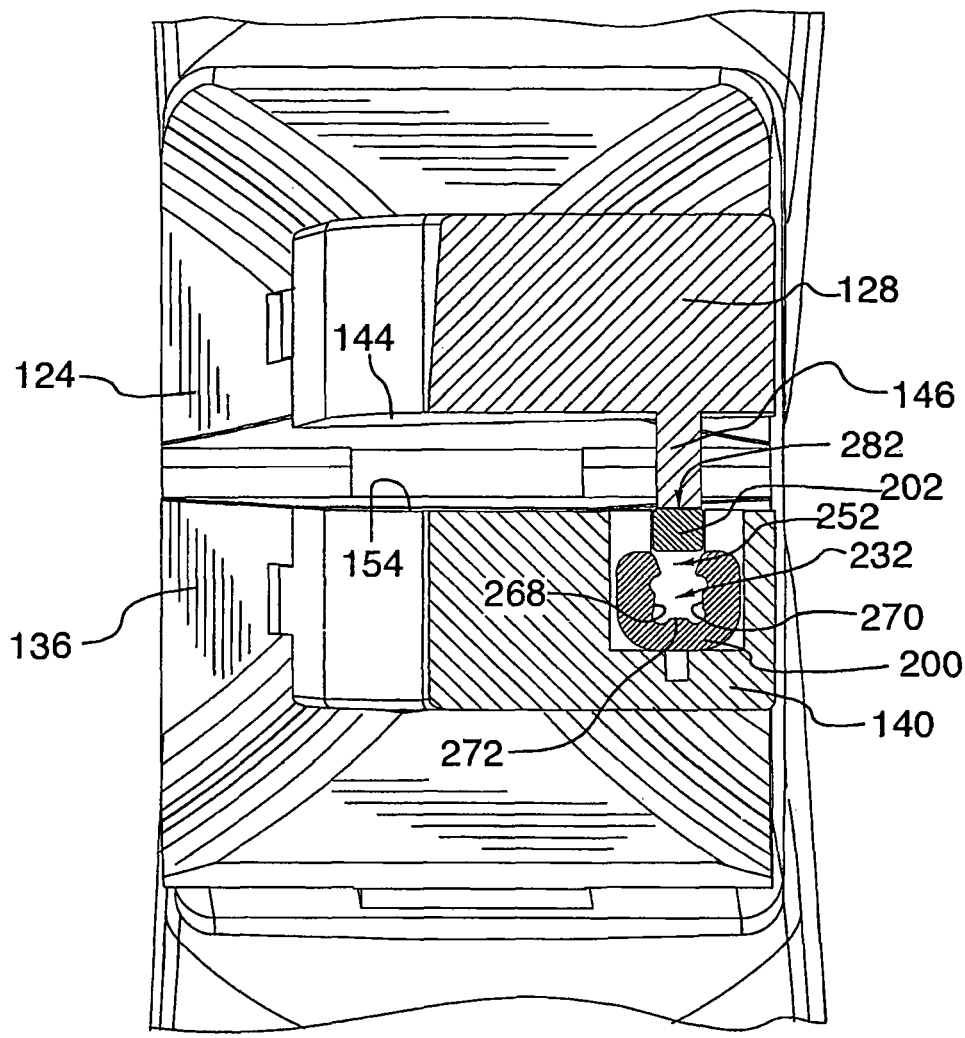
FIG. 16 is an end elevation view looking directly at the work tips of the pliers illustrated in FIG. 6, showing a gripping device of the type shown in FIG. 12 seated in a rebate defined in the female work tip of the pliers and the flange of the male work tip bearing against the outer surface of the arch wire.
Figure 17:
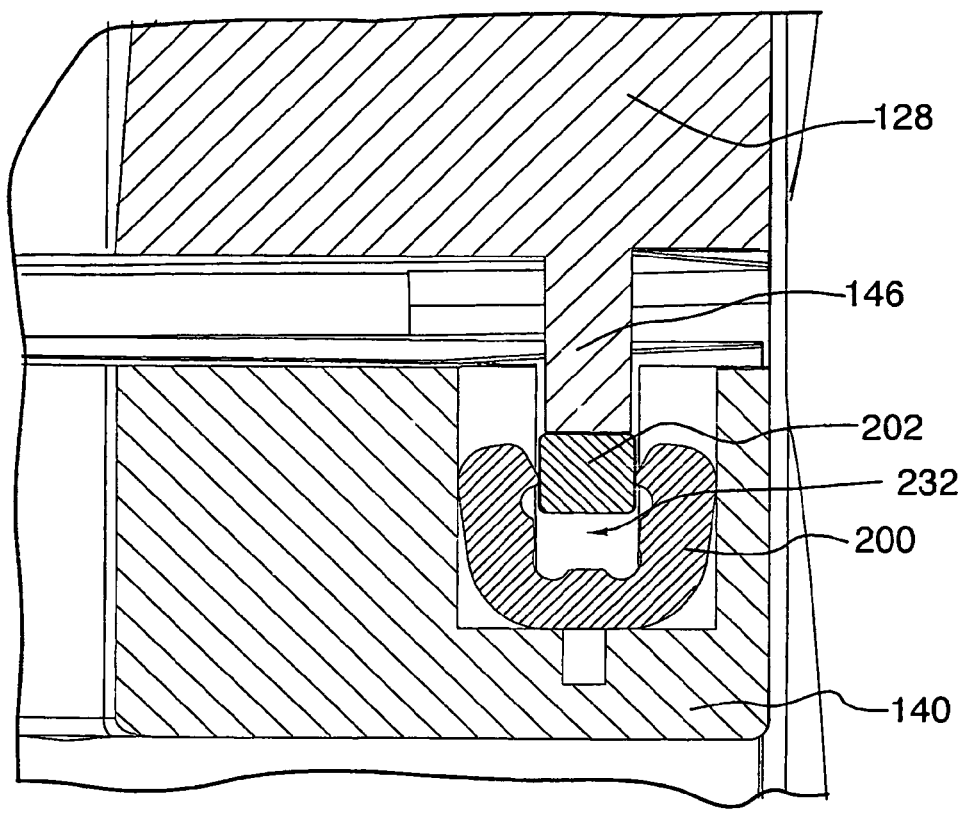
FIG. 17 is magnified elevation view of the work tips and gripping device illustrated in FIG. 16 with a portion of the work tips removed for clarity, with the arm portions of the gripping device shown deflecting outwardly from each other as the arch wire is admitted through the entranceway of the gripping device body.

The orthodontist then squeezes the handle portions 122 and 134 together thereby causing the flange portion 146 of the first work tip 128 to act upon the section of arch wire 202 to be retained (as best shown in FIG. 16). The flange portion 146 holds the arch wire 202 in place while the second work tip 140 causes the inclined body surfaces 256 and 258 to press against the arch wire. With the application of sufficient force, the arm portions 220 and 222 of the gripping device 200 will begin to deflect outwardly from each other and the throat 254 will widen to accommodate the arch wire 202 therein (see FIG. 17). Once the arch wire 202 has cleared the throat 254, the arm portions 220 and 222 will flex back toward each other in an attempt to return to their original (undeflected) positions. The inner gripping surfaces 268 and 270 of the first and second jaw portions 226 and 230 will come to bear on the lateral faces 284 and 286 of the arch wire 202 and will hold the arch wire 202 tightly within the gripping device 200 thereby discouraging displacement of the arch wire 200 in any direction. With the gripping device 200 now attached to the arch wire 202, the orthodontist can move the arms 112 and 114 of the pliers 110 to the open setting 162 and release the gripping device 200 from the tool.

In the embodiment shown and described, the gripping device 200 is made of nickel titanium, a metal alloy that behaves in a linear superelastic mode. Where the gripping device is a material that behaves in a shape memory mode, the attachment procedure would be similar to that described above.

It will be appreciated that the gripping device 200 could be used with an arch wire having a rectangular cross-section defined by right angle corners. With appropriate modifications the gripping device 200 could also be used with an arch wire of square cross-section (defined by right angle corners or rounded corners). Further still, the principles of the present invention could be applied to design a gripping device suitable for use with arch wires having cross-sections other than circular, rectangular or square. For instance, a gripping device could be configured to clamp onto an arch wire having a generally D-shaped profile (such as, the SPEED D-Wire™ manufactured and sold by Strite Industries Limited of Cambridge, Ontario, Canada), or a profile comprising two right angle corners and one radiused corner (such as, the SPEED Wire™ manufactured and sold by Strite Industries Limited of Cambridge, Ontario, Canada).

In such cases, a gripping device would be made of a superelastic material or shape memory material, beta-titanium III or another suitable material and could be structurally similar to the gripping devices 20 and 200 with an arrangement of arm portions and a base portion. Each arm portion could include a jaw portion, which together with the other jaw portion could form a gripping jaw. The jaw portions could be spaced apart from each other with the gap extending between them sized smaller than the lateral dimension or width of the arch wire. Moreover, the jaw portions could be provided with inner gripping surfaces configured to engage surfaces of the arch wire. In some cases, the profiles of such inner gripping surfaces could be designed to match closely (or correspond to) the shape of the arch wire to be gripped.

Other modifications are possible. In other embodiments, the gripping devices could be provided with means for facilitating handling of the gripping device to better orient or position the gripping device within a pair of pliers or other tool. In one embodiment, such means could take the form of grooves, notches or indents registerable with mating projections on a pair of pliers or other tool. Examples of such embodiments are shown in FIGS. 18 to 21.

Figure 18:
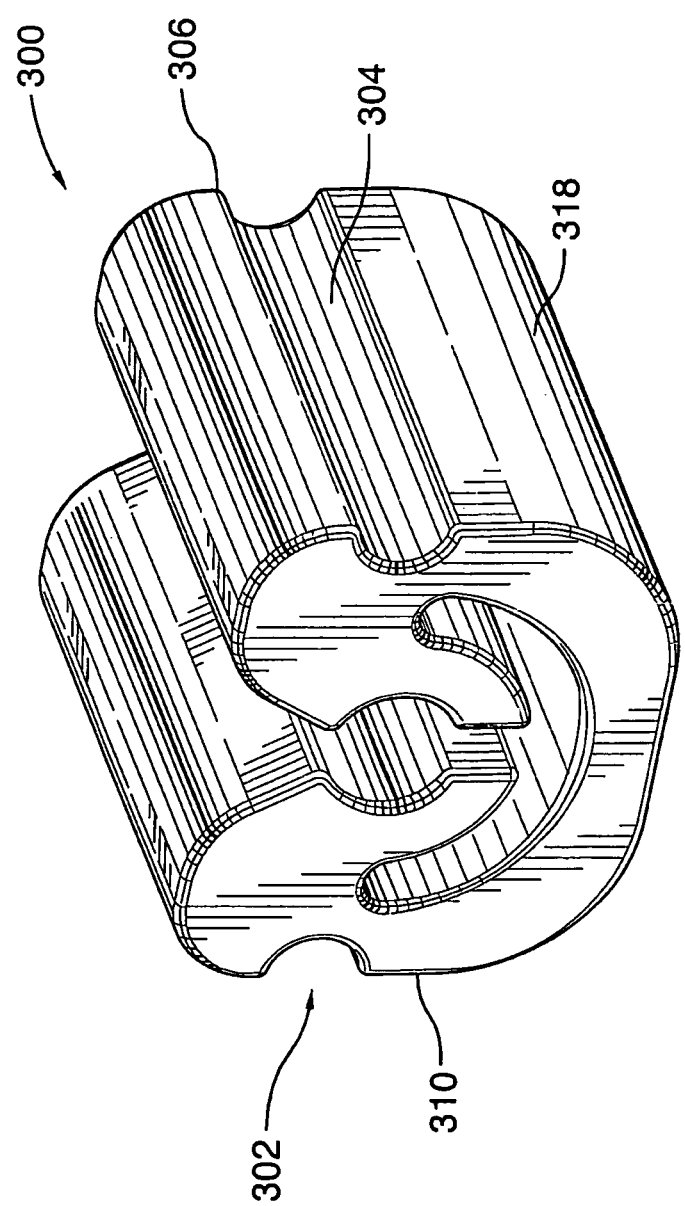
FIG. 18 is a perspective view of an orthodontic gripping device in accordance with a fourth embodiment of the invention.
Figure 19:
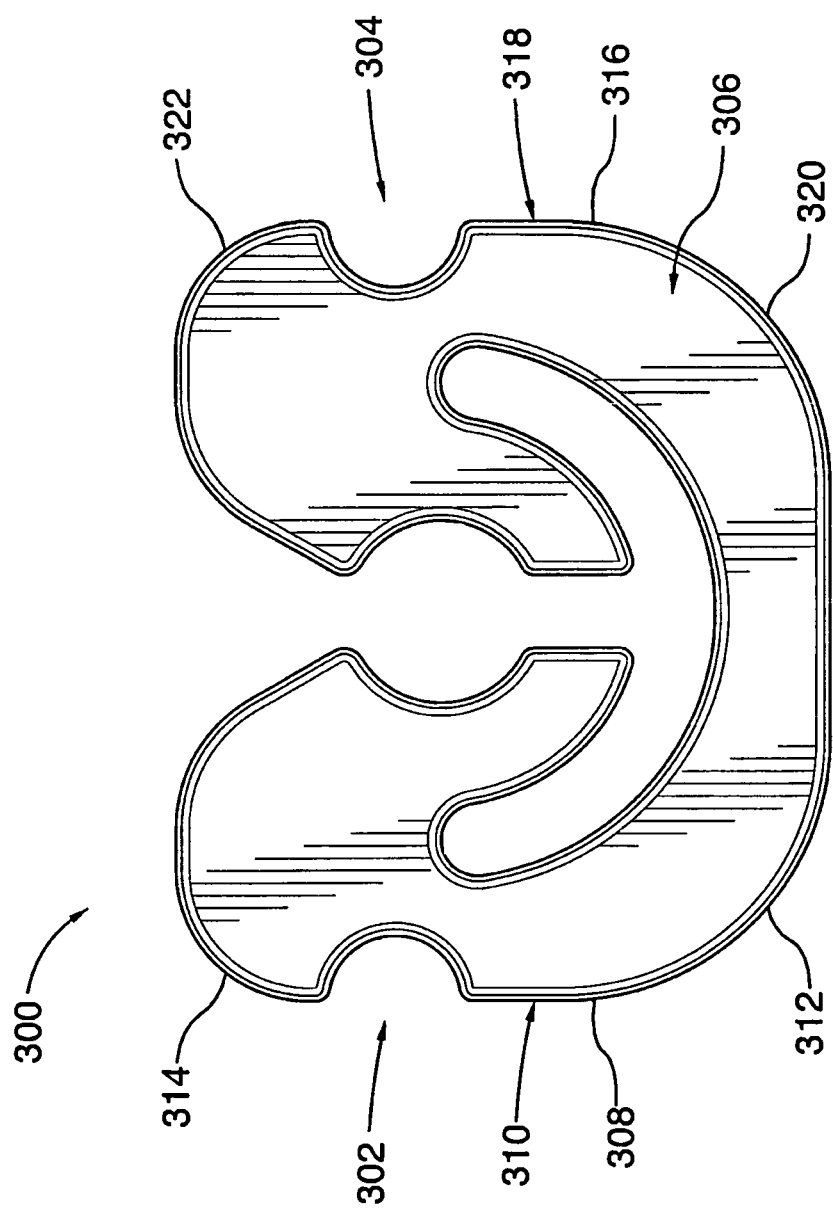
FIG. 19 is an end elevation (or mesial) view of the orthodontic gripping device shown in FIG. 18.

FIGS. 18 and 19 depict a gripping device 300 generally similar to gripping device 20 described above in all material respects except that that gripping device 300 includes a pair of opposed, first and second, elongate grooves or notches 302 and 304 formed on the gripping device body 306. The first groove 302 is defined on the outer surface 308 of the first arm portion 310 and runs the entire length of the body 306. In this embodiment, the first groove 302 is disposed between the first and second corners 312 and 314 of the body 306, closer to second corner 314. Similarly, the second groove 304 is defined on the outer surface 316 of the second arm portion 318 and also runs the entire length of the body 306. The second groove 304 is disposed between the third and fourth corners 320 and 322 of the body 306, closer to fourth corner 322. In this embodiment, the grooves 302 and 304 have an arcuate profile. In other embodiments, the grooves could have a different profile and be arranged differently. For instance, in other embodiments, the grooves could be made to extend only partway along the body. The grooves could be formed closer to the base portion. Alternatively, the outer surface of each arm portion could be provided with more than one groove. In still other embodiments, the means for facilitating handling of the gripping device could take a different form. For example, instead of providing grooves on the gripping device body which are registerable with projections on a tool, the gripping device body could be provided with projections which mate with grooves formed on the work tip surface of the tool.

Figure 20:
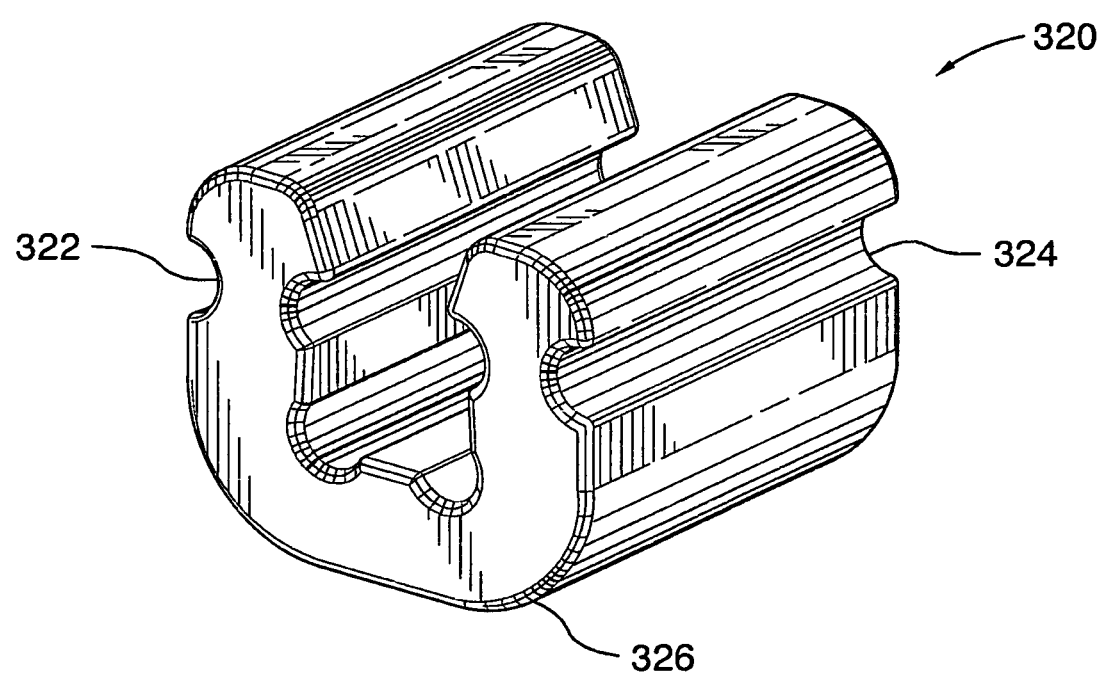
FIG. 20 is a perspective view of an orthodontic gripping device in accordance with a fifth embodiment of the invention.
Figure 21:
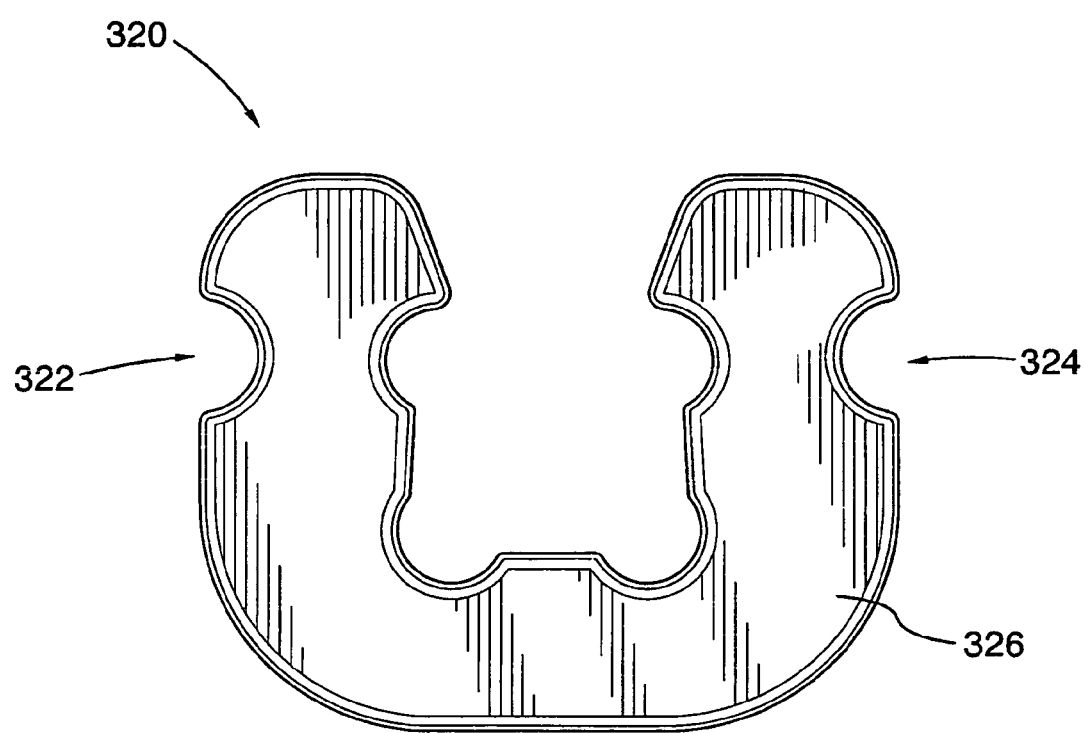
FIG. 21 is an end elevation (or mesial) view of the orthodontic gripping device shown in FIG. 20.

FIGS. 20 and 21 show a gripping device 320 generally similar to gripping device 200 described above in all material respects except that the gripping device 320 includes a pair of opposed, first and second, elongate grooves or notches 322 and 324 formed on the gripping device body 326. The configuration of the grooves 322 and 324 and their arrangement on the body 326 is generally similar to the configuration of grooves 302 and 304 and their arrangement on body 306 such that no further description is required.

Figure 22:
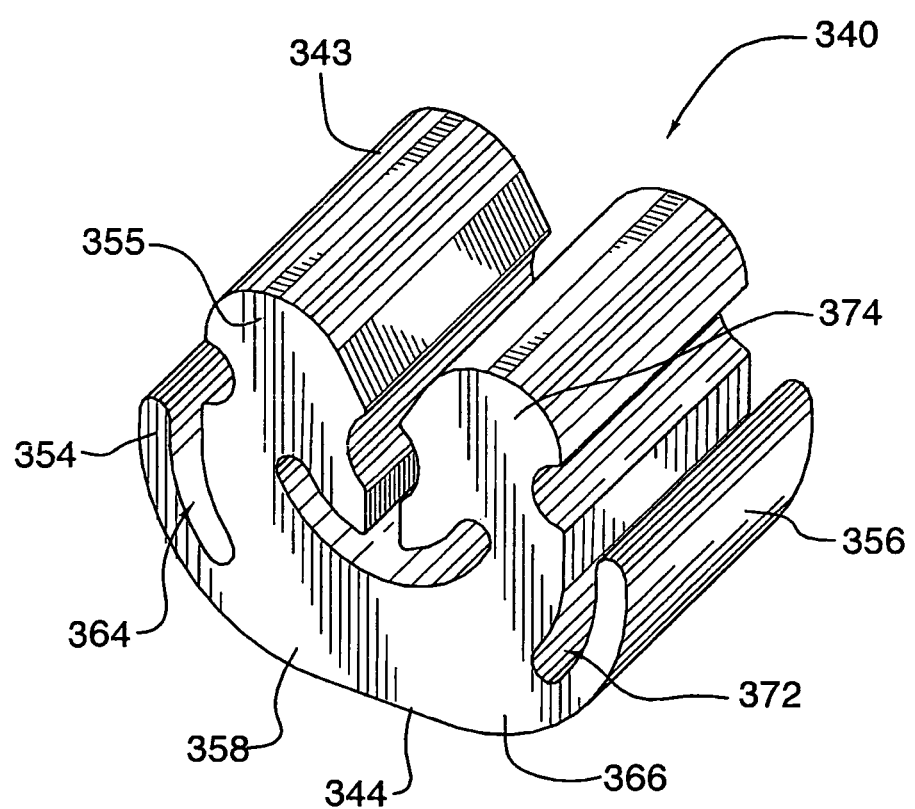
FIG. 22 is a perspective view of an orthodontic gripping device in accordance with a sixth embodiment of the invention.
Figure 23:
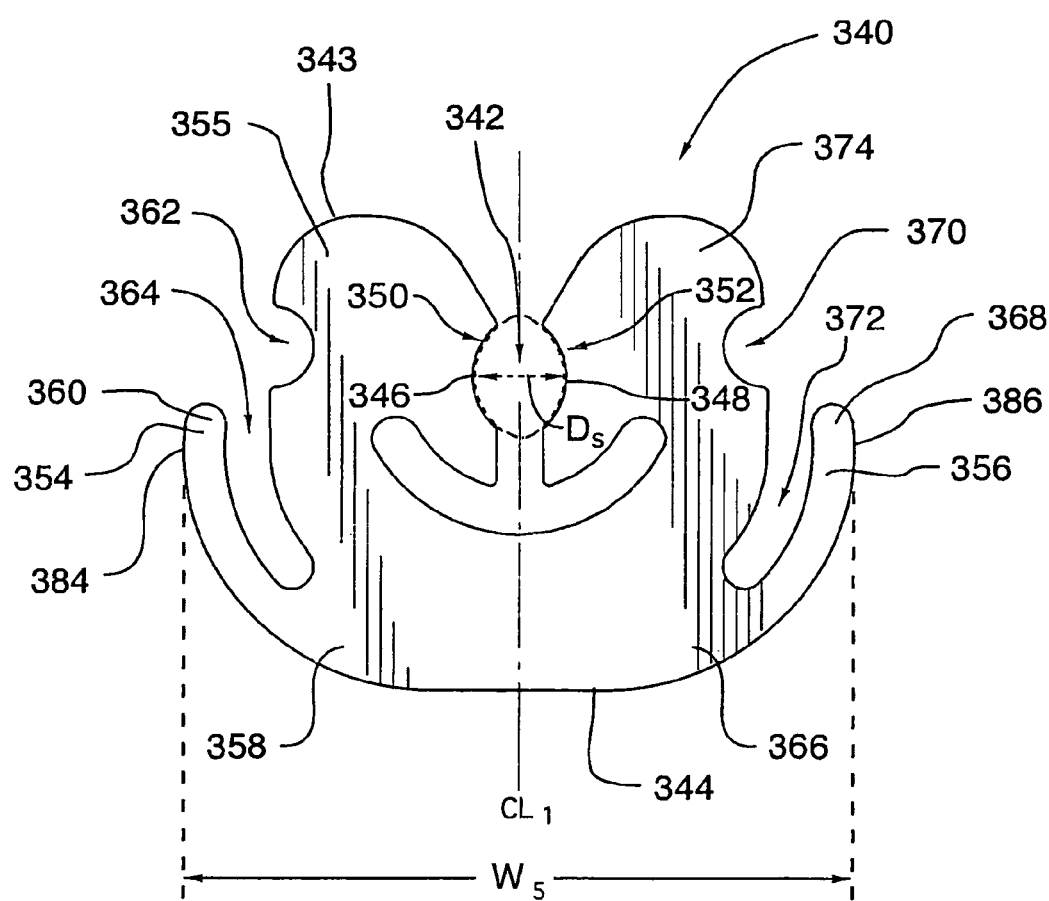
FIG. 23 is an end elevation (or mesial) view of the orthodontic gripping device shown in FIG. 22.

FIGS. 22 and 23 show a gripping device 340 in accordance with a sixth embodiment of the present invention. The gripping device 340 is generally similar to gripping device 300 described above in all material respects except that the gripping device 340 has an arch wire receiving station 342 that is configured differently than the arch wire receiving station of gripping device 300 and the gripping device 340 includes a different body 343 with a somewhat reinforced (or thicker) base portion 344 than the base portion of the gripping device 300.

More specifically, in contrast to the arch wire receiving station of the gripping device 300 which has a circular profile (not unlike arch wire receiving station 48 shown in FIG. 2A), the arch wire receiving station 342 has an oval or elliptical profile (demarcated by dashed lines in FIG. 23). The oval profile is defined substantially by opposed inner gripping surfaces 346 and 348 of the first and second jaw portions 350 and 352, respectively. In this embodiment, the major axis of the oval profile is aligned with the longitudinal centerline $CL_1$. In other embodiments, the major axis could be disposed parallel to, but offset from, the longitudinal centerline $CL_1$.

By virtue of the oval profile of the arch wire receiving station 342, the centre point for the radius of curvature of the inner gripping surface 346 is offset from the centre point for the radius of curvature of the inner gripping surface 348, and both centre points are offset from the longitudinal centreline $CL_1$.

The arch wire receiving station 342 has a short diameter $D_s$ (i.e. the diameter measured along its minor axis) defined by the opposing inner gripping surfaces 346 and 348. The diameter $D_s$ of the arch wire receiving station 342 is sized slightly smaller than the diameter $D_1$ of the arch wire 50. Preferably, the diameter $D_s$ is sized between about 10% to about 15% smaller than the diameter $D_1$. In other embodiments, the sizing of diameter $D_s$ may differ.

It has been found that by configuring the arch wire receiving station 342 with an oval profile enhanced gripping forces may be generated when an arch wire of circular or substantially circular cross-section is placed in the gripping device 340.

In this embodiment, the base portion 344 is more prominent than the base portion of the gripping device 300 in order to support a pair of first and second, lateral wing members (or deflectable fingers) 354 and 356 which depend from, and are integrally formed with, the base portion 344. The first lateral wing member 354 extends from the corner portion 358 of the gripping device body 343 substantially in the direction of the arch wire receiving station 342 in a curved, finger-like fashion. The first lateral wing member 354 terminates at a free end 360 which stops shy of an elongate groove or notch 362 defined in the gripping device body 343 so as not obstruct access thereto. The notch 362 is similar in structure and purpose to notch 302 formed in gripping device body 306. Defined between the first lateral wing member 354 and the first arm portion 355 of the gripping device body 343 is an elongate gap 364.

Similarly, the lateral wing member 356 extends from the corner portion 366 of the gripping device body 343 substantially in the direction of the arch wire receiving station 342 in a curved, finger-like fashion. The lateral wing member 356 terminates at a free end 368 which stops shy of an elongate groove or notch 370 defined in the gripping device body 343 so as not obstruct access thereto. The notch 370 is similar in structure and purpose to notch 304 formed in gripping device body 306. An elongate gap 372, similar to gap 364, extends between the lateral wing member 356 and the second arm portion 374 of the gripping device body 343. As will be explained in greater detail below, the gaps 364 and 372 provide a clearance for the lateral wing members 354 and 356 to allow them to move between their respective undeflected positions 380 and their respective deflected positions 382.

In other embodiments, the lateral wing members could be configured differently.

Figure 24A:
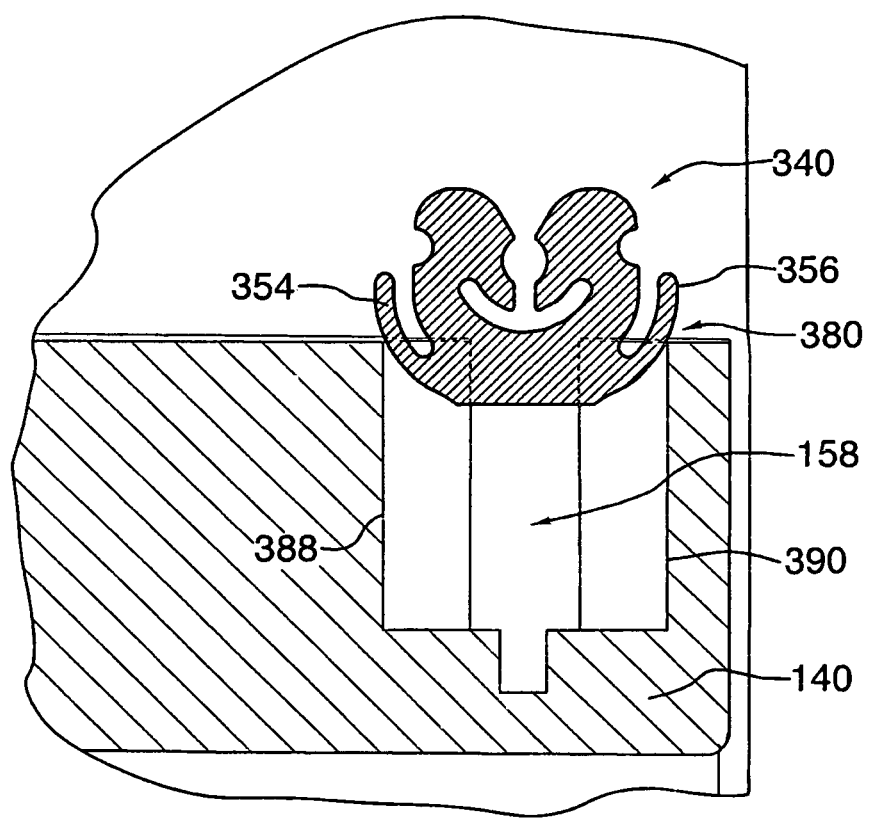
FIG. 24A is a magnified elevation view similar to that illustrated in FIG. 11 showing the female work tip only of the orthodontic pliers and the gripping device of FIG. 23 with the lateral wing members of the gripping device occupying their respective undeflected positions, prior to insertion of the gripping device into the rectangular rebate of the female work tip.
Figure 24:
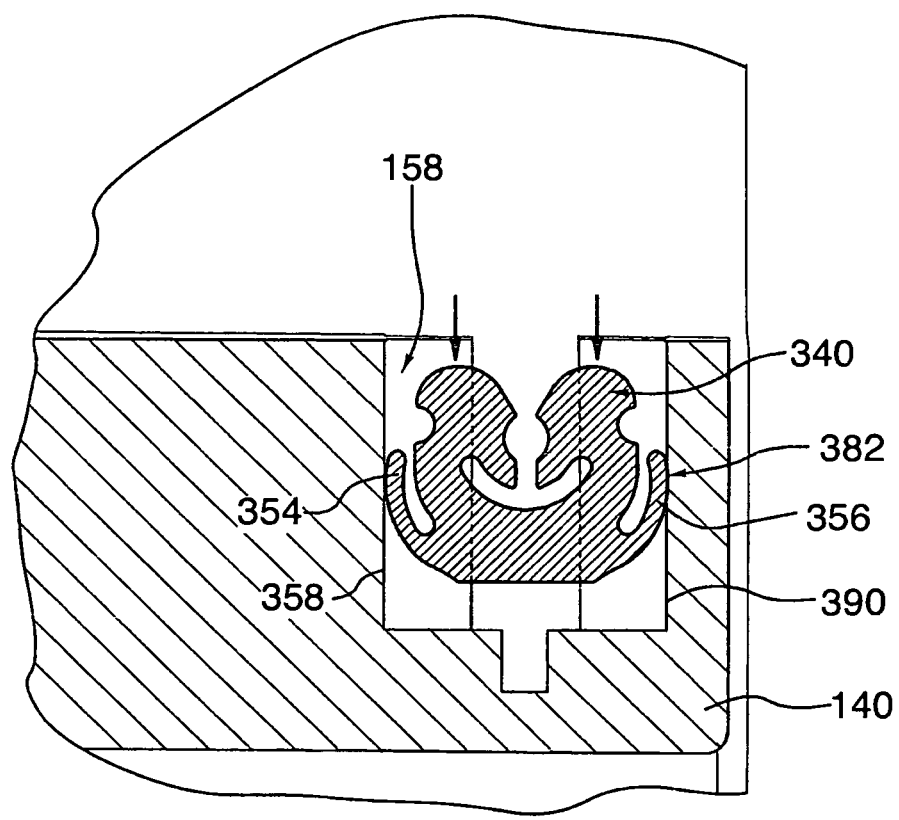
FIG. 24B is a magnified elevation view of the female work tip and the gripping device illustrated in FIG. 24A showing the lateral wing members of the gripping device moved to their respective deflected positions thereby allowing the gripping device to fit within the rectangular rebate of the female tip portion.

The purpose of the lateral wing members 354 and 356 is to facilitate handling of the gripping device 340 by an orthodontist using the orthodontic pliers 110 described earlier (or the like). More specifically and as shown in FIGS. 24A and 24B, the lateral wing members 354 and 356 serve as resilient stops for preventing the accidental release of the gripping device 340 when it is seated within the rectangular rebate 158 formed in the second work tip 140 of the pliers 110.

When the lateral wing members 354 and 356 are in their respective undeflected positions 380 (shown in FIGS. 23 and 24A), the gripping device 340 has a width $W_5$ (as measured between the outer lateral surface 384 of the first lateral wing member 354 and the outer lateral surface 386 of the second lateral wing member 356) that is larger than the width of the rectangular rebate 158. Conversely, when a force is applied on the gripping device 340 (either manually by the orthodontist using his/her finger, or mechanically, using the flange 146 formed on the first work of the pliers 110), the lateral wing members 354 and 356 are urged to move to their respective deflected positions 382 (shown in FIG. 24B), wherein the free ends 360 and 368 encroach onto the gaps 364 and 372 such that the width $W_5$ is slightly smaller than the width of the rectangular rebate 158. This allows the gripping device 340 to be accommodated and captively retained within the rebate 158.

Because the orthodontic gripping device 340 is made from a superelastic metal alloy, the lateral wing members 354 and 356 are resilient and biased to their original (undeflected) positions 380. As lateral wing members 354 and 356 seek to return to their original positions, the outer lateral surfaces 384 and 386 of the lateral wing members 354 and 356 are urged against the walls 388 and 390 which define the rectangular rebate 158, exerting an outward force thereupon. It is these forces which operate to retain the gripping device within the rectangular rebate 158.

The attachment of the orthodontic gripping device 340 to an arch wire is generally similar to the attachment of the gripping device 20 to arch wire 50 described above such that no further description is required.

Figure 25:
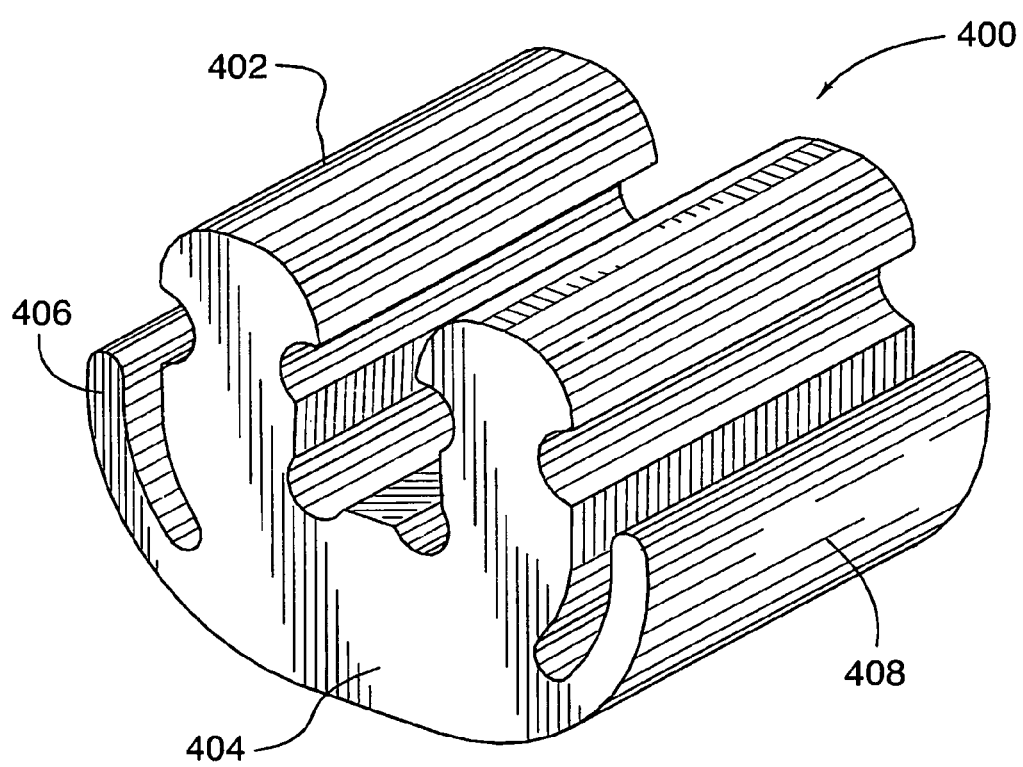
FIG. 25 is a perspective view of an orthodontic gripping device in accordance with a seventh embodiment of the invention.
Figure 26:
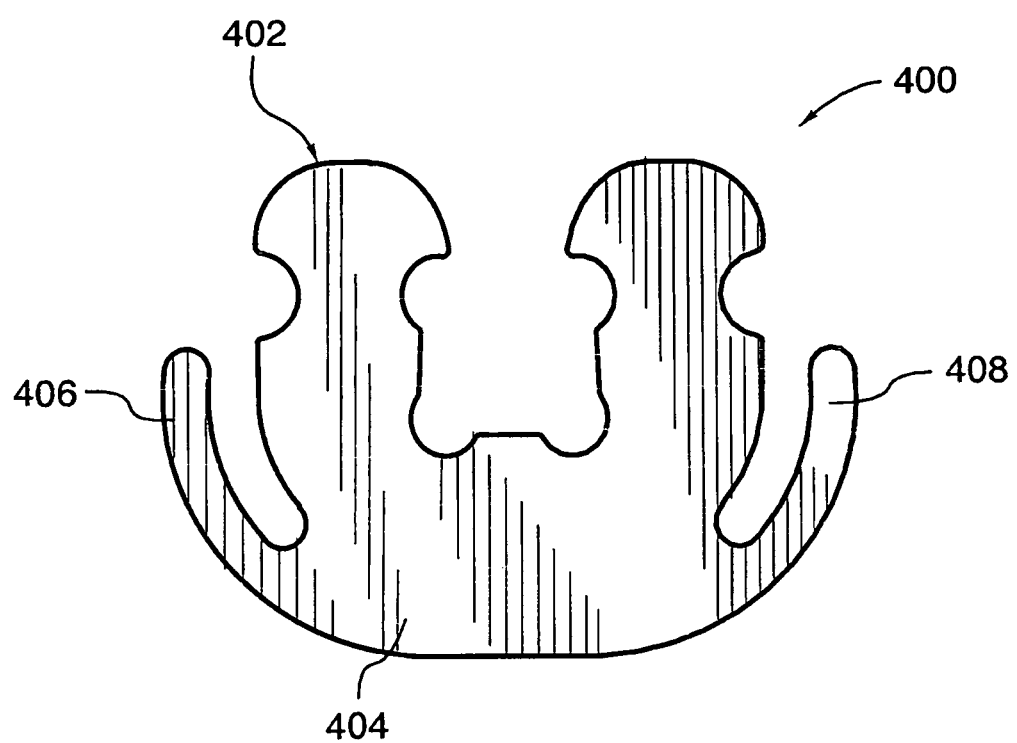
FIG. 26 is an end elevation (or mesial) view of the orthodontic gripping device shown in FIG. 25.

FIGS. 25 and 26 show a gripping device 400 generally similar to gripping device 320 described above in all material respects except that the gripping device 400 includes a different body 402 with a somewhat reinforced (or thicker) base portion 404 from which depend a pair of first and second lateral wing members 406 and 408. In this regard, the structure of the base portion 404 and the configuration and arrangement of the lateral wing members 406 and 408 generally resembles those of the base portion 344 and the lateral wing members 354 and 356 such that the description of the latter elements will suffice for the former elements.

It will be appreciated that the gripping devices shown in FIGS. 2A and 13A could also be constructed with thickened base portions and lateral wing members as described above.

In the embodiments shown in FIGS. 1 to 5 and 12 to 15, 18 to 23, 25 and 26, the gripping devices all have a split-body configuration particularized by a funnel-shaped entranceway leading into the body and providing access to the arch wire receiving station. In other embodiments, the gripping device body could be shaped differently. In one alternative embodiment, the gripping device body could have an annular or donut shaped body with spaced apart, deflectable arm portions (similar to those described above in the context of the other embodiments shown in the figures) contained within the envelope of the annular body. In such cases, the entranceway would be defined by the apertures defined in the mesial and distal faces of the body giving access to the arch wire receiving station. The gripping device could be placed onto the arch wire by urging the tip of the arch wire through the arch wire receiving station.

Any of the arch wire gripping devices described above or other arch wire gripping devices constructed in accordance with the principles of the present invention could be provided with accessories in the form of a hook (such as hook 172, shown in FIG. 5A), an auxiliary slot, an eyelet, or the like.

Any of the arch wire gripping devices described above or other arch wire gripping devices constructed in accordance with the principles of the present invention could be used as end stops (i.e. to restrict displacement at the ends of the arch wire). Alternatively, the gripping devices could be employed to resist displacement of a particular bracket/tooth arrangement relative to the arch wire.

The foregoing disclosure has described exemplary uses of gripping devices with arch wires. While gripping devices made in accordance with the principles of the present invention tend to be well-suited for use in conjunction with arch wires, it should be appreciated that use of the gripping device is not limited to arch wires. Gripping devices constructed in accordance with the principles of the present invention could be employed to similar advantage in conjunction with wires other than arch wires or further still, with auxiliary dental devices or other dental components needing to be gripped or tightly retained. Moreover, the principles of the present invention need not be restricted solely to dental/orthodontic applications. With appropriate modifications, the gripping devices described above could be adapted for gripping objects other than arch wires or dental components.

Although the foregoing description and accompanying drawings relate to specific preferred embodiments of the present invention as presently contemplated by the inventor, it will be understood that various changes, modifications and adaptations, may be made without departing from the spirit of the invention.

What is claimed is:

1. An orthodontic arch wire stop for attaching to an arch wire, the arch wire stop comprising:
   a body made of a material selected from the group consisting of a superelastic metal alloy, cold worked titanium beta III, and solution heat treated and aged titanium beta III; the body having a base portion, and first and second, spaced apart arm portions connected to each other by way of the base portion; the first arm portion including a first jaw portion having a first inner, arch wire-gripping surface; the second arm portion including a second jaw portion having a second inner, arch wire-gripping surface; the first and second inner gripping surfaces being disposed opposite one another in spaced relation, the space between the first and second inner gripping surfaces defining a station for receiving the arch wire therein, at least a portion of the arch wire receiving station being sized smaller than the arch wire;

the body further including:
an entranceway defined between the first and second arm portions, the entranceway providing access to the arch wire receiving station; and
a passageway formed in the body in communication with the arch wire receiving station; the passageway being disposed between the base portion and the arch wire receiving station such that the arch wire receiving station is spaced away from the base portion;
an arcuate cutout defined in the body between the first and second arm portions and the base portion; the arcuate cutout communicating with the passageway;
the first and second arm portions being resiliently deflectable outwardly away from each other when the arch wire is admitted through the entranceway into the arch wire receiving station;
the first and second inner gripping surfaces configured to engage the arch wire and apply opposing gripping forces against the arch wire so as to arrest displacement of the arch wire stop relative to the arch wire in at least a mesial or distal direction, when the arch wire is seated within the arch wire receiving station.

2. The arch wire stop of claim 1 wherein the body is of unitary construction.

3. The arch wire stop of claim 1 wherein the first and second arm portions are not integrally formed with each other.

4. The arch wire stop of claim 1 wherein the material is a superelastic metal alloy selected from the group consisting of: (a) cold worked nickel titanium; (b) cold worked and aged nickel titanium; (c) cold worked nickel titanium and other alloying elements; and (d) cold worked and aged nickel titanium and other alloying elements.

5. The arch wire stop of claim 1 wherein the material is a superelastic metal alloy that behaves in a linear superelastic mode.

6. The arch wire stop of claim 1 wherein the material is a superelastic metal alloy that behaves in a non-linear superelastic mode.

7. The arch wire stop of claim 1 wherein the body is made of a material consisting of: (a) cold worked titanium beta III; and (b) solution heat treated and aged titanium beta III.

8. The arch wire stop of claim 1 wherein:
the body has a longitudinal centerline;
the first and second arm portions are disposed on opposite sides of the longitudinal centerline; and
the first and second arm portions are mirror images of each other.

9. The arch wire stop of claim 1 wherein the body has a longitudinal centerline and the body is symmetrical about the longitudinal centerline.

10. The arch wire stop of claim 1 wherein the body has a longitudinal centerline and the body is asymmetrical about the longitudinal centerline.

11. The arch wire stop of claim 1 wherein the body has a transverse centerline and the body is symmetrical about the transverse centerline.

12. The arch wire stop of claim 1 wherein the body has a transverse centerline and the body is asymmetrical about the transverse centerline.

13. The arch wire stop of claim 1 wherein the entranceway is disposed opposite the base portion.

14. The arch wire stop of claim 1 wherein:
the first and second gripping surfaces are configured to substantially conform to at least a portion of the outer surface of the arch wire.

15. The arch wire stop of claim 14 wherein:
each of the first and second inner gripping surfaces has an arcuate profile configured to match at least partially the arcuate profile of the arch wire.

16. The arch wire stop of claim 1 wherein:
the arch wire receiving station has a substantially circular profile and a diameter; and
the diameter of the arch wire receiving station is sized smaller than the diameter of the arch wire.

17. The arch wire stop of claim 1 wherein each inner gripping surface is a surface selected from the group consisting of: (a) a smooth surface; (b) an irregular surface; (c) a textured surface; and (d) a surface coated with a friction enhancing material.

18. The arch wire stop of claim 1 wherein the entranceway is funnel-shaped and tapers in the direction of the arch wire receiving station.

19. The arch wire stop of claim 18 wherein the entranceway terminates in a throat and the throat is sized smaller than the size of the arch wire.

20. The arch wire stop of claim 19 wherein:
the throat is sized between 35% and 40% of the diameter of the arch wire.

21. The arch wire stop of claim 19 wherein:
the throat is sized between 65% and 70% of the width of the arch wire.

22. The arch wire stop of claim 1 wherein the body has a mesial face and a distal face, and the entranceway is defined by apertures in the mesial and distal faces of the body.

23. The arch wire stop of claim 1 further comprising an orthodontic accessory formed in the body.

24. The arch wire stop of claim 23 wherein the orthodontic accessory is selected from the group consisting of: (a) a hook; (b) an auxiliary slot; and (c) an eyelet.

25. The arch wire stop of claim 1 further comprising a hook extending from the body.

26. The arch wire stop of claim 25 wherein the hook is integrally formed with the body.

27. The arch wire stop of claim 25 wherein the hook is carried on the first arm portion.

28. The arch wire stop of claim 27 wherein the first arm portion has an outer surface and the hook extends perpendicular to the outer surface of the first arm portion.

29. The arch wire stop of claim 25 wherein the first arm portion has an outer surface and die hook extends from the outer surface of the first arm portion on a slant relative to the outer surface.

30. The arch wire stop of claim 25, wherein the hook is carried on the base portion.

31. The arch wire stop of claim 30 wherein the base portion has an outer surface and the hook extends perpendicular to the outer surface of the base portion.

32. The arch wire stop of claim 30 wherein the base portion has an outer surface and the hook extends from the outer surface of the base portion on a slant relative to the outer surface.

33. The arch wire stop of claim 25 wherein the body further includes an outer surface and the hook extends from the outer surface of the body.

34. The arch wire stop of claim 1 wherein the arch wire receiving station is shaped to accommodate an arch wire having a profile selected from the group consisting of: (a) a circular profile and (b) a D-shaped profile.

35. The arch wire stop of claim 1 further comprising means for facilitating handling of the gripping device, the handling facilitating means being formed in the body.

36. The arch wire stop of claim 35 wherein the handling facilitating means includes a first groove defined in an outer surface of the first arm portion and a second groove defined in an outer surface of the second arm portion, the first groove being disposed opposite the second groove.

37. The arch wire stop of claim 35 wherein the handling facilitating means includes first and second lateral wing members extending from the base portion; the first lateral wing member being disposed in spaced relation relative to the first arm portion; and the second lateral wing member being disposed in spaced relation relative to the second arm portion.

38. The arch wire stop of claim 37 wherein:
each of the first and second lateral wing members has an outer lateral surface and is moveable between an undeflected position and a deflected position; and
the gripping device has a width measured between the outer lateral surface of the first lateral wing member and the outer lateral surface of tire second lateral wing member; the width of the gripping device when the first and second lateral wing members are in the deflected position being smaller than the width of the gripping device when the first and second lateral wing members are in the undeflected position.

39. The arch wire stop of claim 1 wherein the arch wire receiving station has a profile selected from the group consisting of: (a) a circular profile and (b) an oval profile.

40. The arch wire stop of claim 1 wherein:
the body has a longitudinal centerline; and
the arch wire receiving station has a substantially oval profile defined by a major axis and a minor axis, the major axis being disposed parallel to the longitudinal centerline.

41. The arch wire stop of claim 40 wherein: the arch wire has a diameter;
the arch wire receiving station has a diameter measured along the minor axis; and the diameter of the arch wire receiving station measured along the minor axis is sized smaller than a diameter of the arch wire.

42. An orthodontic arch wire kit comprising:
an arch wire; and
an arch wire stop for attaching to the arch wire, the arch wire stop comprising:
a body made of a material selected from the group consisting of a superelastic metal alloy, cold worked titanium beta III, and solution heat treated and aged titanium beta III; the body having a base portion, and first and second, spaced apart arm portions connected to each other by way of the base portion; the first arm portion including a first jaw portion having a first inner, arch wire-gripping surface; the second arm portion including a second jaw portion having a second inner, arch wire-gripping surface; the first and second inner gripping surfaces being disposed opposite one another in spaced relation, the space between the first and second inner gripping surfaces defining a station for receiving the arch wire therein, at least a portion of the arch wire receiving station being sized smaller than the arch wire;
the body further including:
an entranceway defined between the first and second arm portions, the entranceway providing access to the arch wire receiving station; and
a passageway formed in the body in communication with the arch wire receiving station; the passageway being disposed between the base portion and the arch wire receiving station such that the arch wire receiving station is spaced away from the base portion;
an arcuate cutout defined in the body between the first and second arm portions and the base portion; the arcuate cutout communicating with the passageway;
the first and second arm portions being resiliently deflectable outwardly away from each other when the arch wire is admitted through the entranceway into the arch wire receiving station;
the first and second inner gripping surfaces configured to engage the arch wire and apply opposing gripping forces against the arch wire so as to arrest displacement of the arch wire stop relative to the arch wire in at least a mesial or distal direction, when the arch wire is seated within the arch wire receiving station.

43. The kit of claim 42 wherein the arch wire has a cross-sectional profile selected from the group consisting from: (a) circular and (b) D-shaped.

44. The kit of claim 42 wherein the arch wire is formed from wire strands selected from the group consisting of: (a) braided wire strands; and (b) helically wrapped wire strands.

45. The kit of claim 42 wherein the arch wire is selected from the group consisting of: (a) a multi-strand arch wire with a core; and (b) a multi-strand coreless arch wire.

46. The kit of claim 42 wherein the arch wire is a single solid wire.

47. The kit of claim 42 wherein the arch wire is made of material selected from the group consisting of: (a) a linear elastic material; (b) a superelastic material; and (c) a shape memory material.

48. A dental gripping device for attaching to a dental component, the gripping device comprising:
a body made of a material selected from the group consisting of a superelastic metal alloy, cold worked titanium beta III, and solution heat treated and aged titanium beta III; the body having a base portion, and first and second, spaced apart arm portions connected to each other by way of the base portion; the first arm portion including a first jaw portion having a first inner gripping surface; the second arm portion including a second jaw portion having a second inner gripping surface; the first and second inner gripping surfaces being disposed opposite one another in spaced relation, the space between the first and second inner gripping surfaces defining a station for receiving the dental component therein, at least a portion of the receiving station being sized smaller than the dental component;
the body further including:
an entranceway defined between the first and second arm portions, the entranceway providing access to the receiving station; and
a passageway formed in the body in communication with the receiving station; the passageway being disposed between the base portion and the receiving station such that the receiving station is spaced away from the base portion;

an arcuate cutout defined in the body between the first and second arm portions and the base portion; the arcuate cutout communicating with the passageway;

the first and second arm portions being resiliently deflectable outwardly away from each other when the dental component is admitted through the entranceway into the receiving station;

the first and second inner gripping surfaces configured to engage the dental component and apply opposing gripping forces against the dental component so as to arrest lateral displacement of the gripping device relative to the dental component, when the dental component is seated within the receiving station.

49. A gripping device for attaching to an object to be gripped, the gripping device comprising:

a body made of a material selected from the group consisting of a superelastic metal alloy, cold worked titanium beta III, and solution heat treated and aged titanium beta III; the body having a base portion, and first and second, spaced apart arm portions connected to each other by way of the base portion; the first arm portion including a first jaw portion having a first inner gripping surface; the second arm portion including a second jaw portion having a second inner gripping surface; the first and second inner gripping surfaces being disposed opposite one another in spaced relation, the space between the first and second inner gripping surfaces defining a station for receiving the object to be gripped therein, at least a portion of the receiving station being sized smaller than the object to be gripped;

the body further including:

an entranceway defined between the first and second arm portions, the entranceway providing access to the receiving station; and a passageway formed in the body in communication with the receiving station; the passageway being disposed between the base portion and the receiving station such that the receiving station is spaced away from the base portion;

an arcuate cutout defined in the body between the first and second arm portions and the base portion; the arcuate cutout communicating with the passageway;

the first and second arm portions being resiliently deflectable outwardly away from each other when the object to be gripped is admitted through the entranceway into the receiving station;

the first and second inner gripping surfaces configured to engage the object to be gripped and apply opposing gripping forces against the object to be gripped so as to arrest lateral displacement of the gripping device relative to the object to be gripped, when the object to be gripped is seated within the receiving station.

* * * * *